(12) United States Patent
Rodrigues et al.

(10) Patent No.: US 9,540,473 B2
(45) Date of Patent: Jan. 10, 2017

(54) RHEOLOGY MODIFIERS

(71) Applicant: Akzo Nobel Chemicals International B.V., Amersfoort (NL)

(72) Inventors: Klin Aloysius Rodrigues, Signal Mountain, TN (US); Anthony John Adamo, Flagtown, NJ (US); Samuel Anthony Vona, Jr., Highland, NY (US)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 14/772,946

(22) PCT Filed: Mar. 10, 2014

(86) PCT No.: PCT/EP2014/054515
§ 371 (c)(1),
(2) Date: Sep. 4, 2015

(87) PCT Pub. No.: WO2014/139904
PCT Pub. Date: Sep. 18, 2014

(65) Prior Publication Data
US 2016/0017079 A1    Jan. 21, 2016

Related U.S. Application Data

(60) Provisional application No. 61/778,584, filed on Mar. 13, 2013.

(30) Foreign Application Priority Data

Jul. 4, 2013    (EP) .................................... 13175109

(51) Int. Cl.
*C08F 2/00* (2006.01)
*C08F 20/10* (2006.01)
(Continued)

(52) U.S. Cl.
CPC ............ *C08F 251/02* (2013.01); *A61K 8/8135* (2013.01); *A61K 8/8152* (2013.01); *A61K 8/8158* (2013.01);
(Continued)

(58) Field of Classification Search
CPC ........... C08F 251/02; C08F 25/00; C08L 1/28; C08L 1/284; C08L 1/286; C08L 3/02; C08L 3/04; C08L 3/10; C08L 5/16; C08L 33/064; C08L 1/02; C08L 33/08; C08L 33/10; C08L 33/12; C09D 151/02; C09D 133/02; C09D 133/26; C09D 135/00; A61Q 19/00; A61K 8/8135; A61K 8/8158; A61K 2800/48; A61K 2800/548
(Continued)

(56) References Cited

U.S. PATENT DOCUMENTS 3,883,453 A    5/1975    Takahashi et al.
4,874,604 A    10/1989   Sramek
(Continued)

FOREIGN PATENT DOCUMENTS

CN    102549034 A    7/2012
EP     0055056 A1    6/1982
(Continued)

OTHER PUBLICATIONS

European Search Report for EP 13175109.1, dated Jul. 8, 2013.
International Search Report and Written Opinion for PCT/EP2014/054515, date of mailing Apr. 23, 2014.

*Primary Examiner* — William Cheung
(74) *Attorney, Agent, or Firm* — Sandra B. Weiss

(57) ABSTRACT

Polysaccharide alkali swellable rheology modifiers include an emulsion polymer including at least one polysaccharide portion and at least one synthetic portion wherein the at least (Continued)

one synthetic portion is obtained from at least one anionic ethylenically unsaturated monomer, at least one nonionic ethylenically unsaturated monomer or a combination thereof; wherein at least one of the nonionic ethylenically unsaturated monomers is a hydrophobic ethylenically unsaturated monomer, as well as methods of making polysaccharide alkali swellable rheology modifiers.

17 Claims, 2 Drawing Sheets

(51) Int. Cl.
| | | |
|---|---|---|
| C08F 251/02 | (2006.01) | |
| C08L 1/02 | (2006.01) | |
| C08L 1/28 | (2006.01) | |
| C08L 3/02 | (2006.01) | |
| C08L 3/04 | (2006.01) | |
| C08L 3/10 | (2006.01) | |
| C08L 5/16 | (2006.01) | |
| C08L 33/06 | (2006.01) | |
| C09D 133/02 | (2006.01) | |
| C09D 133/26 | (2006.01) | |
| C09D 135/00 | (2006.01) | |
| C09D 151/02 | (2006.01) | |
| A61Q 19/00 | (2006.01) | |
| A61K 8/81 | (2006.01) | |
| C08F 251/00 | (2006.01) | |

(52) U.S. Cl.
CPC ............ *A61Q 19/00* (2013.01); *C08F 251/00* (2013.01); *C08L 1/02* (2013.01); *C08L 1/28* (2013.01); *C08L 1/284* (2013.01); *C08L 1/286* (2013.01); *C08L 3/02* (2013.01); *C08L 3/04* (2013.01); *C08L 3/10* (2013.01); *C08L 5/16* (2013.01); *C08L 33/064* (2013.01); *C09D 133/02* (2013.01); *C09D 133/26* (2013.01); *C09D 135/00* (2013.01); *C09D 151/02* (2013.01); *A61K 2800/48* (2013.01); *A61K 2800/548* (2013.01)

(58) Field of Classification Search
USPC .............................................. 526/200, 318.4
See application file for complete search history.

(56) References Cited

U.S. PATENT DOCUMENTS

| | | |
|---|---|---|
| 5,571,552 A | 11/1996 | Kasica et al. |
| 5,925,722 A | 7/1999 | Exner et al. |
| 6,462,013 B1 | 10/2002 | Cooke, Jr. et al. |
| 2008/0230193 A1* | 9/2008 | Mori ............... B01D 21/01 162/164.1 |
| 2011/0139388 A1 | 6/2011 | Hauschel et al. |
| 2012/0302489 A1 | 11/2012 | Rodrigues et al. |

FOREIGN PATENT DOCUMENTS

| | | | |
|---|---|---|---|
| WO | 2013/064647 | A1 | 5/2013 |
| WO | 2013/064648 | A1 | 5/2013 |

* cited by examiner

Sample with Polymer of Example 1

Sample without Polymer of Example 1

RHEOLOGY MODIFIERS

This application is a national stage filing under 35 U.S.C. §371 of PCT/EP2014/054515, filed Mar. 10, 2014, which claims priority to U.S. Provisional Patent Application No. 61/778,584, filed Mar. 13, 2013, and European Patent Application No. 13175109.1, filed Jul. 4, 2013, the contents of which are each incorporated herein by reference in their entireties.

FIELD OF THE INVENTION

The present invention relates to rheology modifiers. More specifically, the present invention relates to polysaccharide alkali swellable rheology modifiers.

BACKGROUND

Rheology modifiers are used in a variety of personal care and industrial applications. Most of the conventional rheology modifiers are produced from petrochemical based raw materials. Accordingly, there is a need to produce rheology modifiers that are at least partly derived from renewable raw materials.

One of the benefits of rheology modifiers is their ability to suspend solid materials in aqueous systems. Suspension benefits are usually obtained by using crosslinked polyacrylic acids, such as carbomer-type polymers. These crosslinked polyacrylic acid-based materials are conventionally made in a solvent and therefore are not considered environmentally friendly, or "green". Accordingly, there is a need to provide more environmentally, or "greener", rheology modifiers and in particular such rheology modifiers that can deliver suspension benefits to a variety of formulations.

SUMMARY OF THE INVENTION

In an aspect, the invention is directed to a polysaccharide alkali swellable rheology modifier comprising an emulsion polymer comprising at least one polysaccharide portion and at least one synthetic portion. The synthetic portion is obtained from at least one anionic ethylenically unsaturated monomer and at least one nonionic ethylenically unsaturated monomer. At least one of the nonionic ethylenically unsaturated monomers is a hydrophobic ethylenically unsaturated monomer.

In another aspect, the invention is directed to a method of making a polysaccharide alkali swellable rheology modifier. The method comprises emulsion polymerizing a polysaccharide, at least one anionic ethylenically unsaturated monomer and at least one nonionic ethylenically unsaturated monomer in the presence of an initiating system. At least one of the nonionic ethylencially unsaturated monomers is a hydrophobic ethylenically unsaturated monomer. The hydrophobic ethylenically unsaturated monomer is present in an amount effective to form an emulsion.

BRIEF DESCRIPTION OF THE DRAWING

The invention is best understood from the following detailed description when read in connection with the accompanying drawings. Included in the drawings are the following figures.

DETAILED DESCRIPTION OF THE INVENTION

Figure 1:
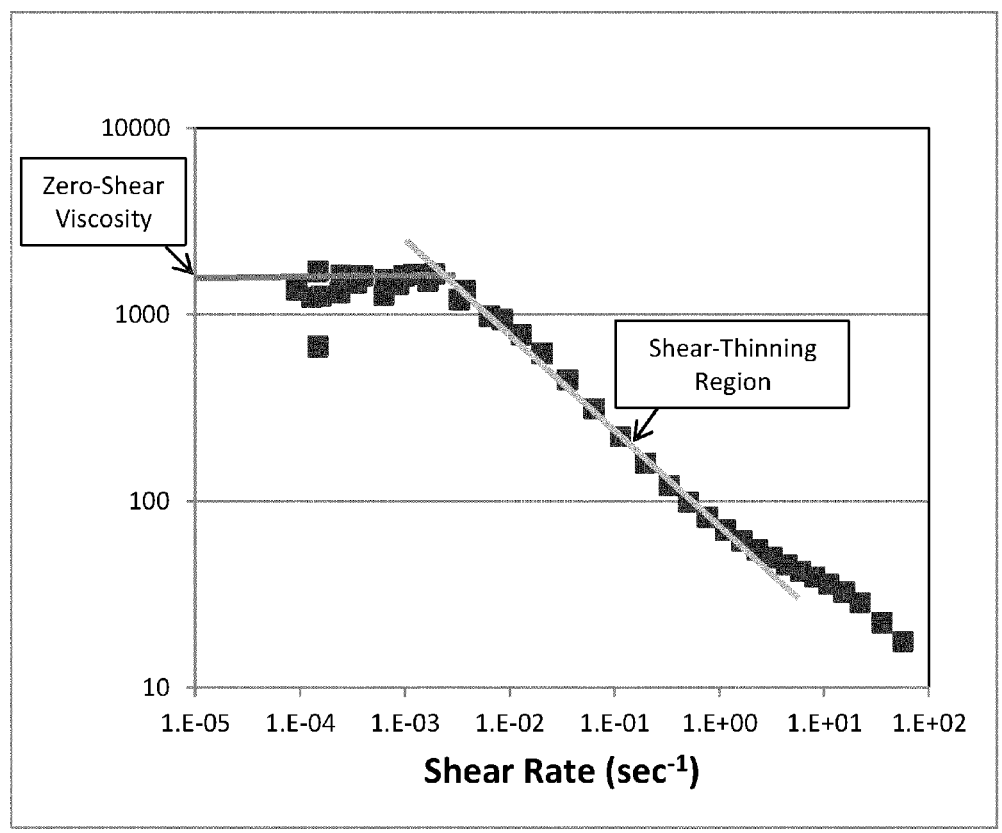
FIG. 1 is an example of a flow curve used in calculating zero-shear obtained by plotting viscosity versus shear rate of the specified samples.

The invention generally relates to rheology modifiers that are alkali swellable. For purposes of the present invention, "polysaccharide alkali swellable rheology modifier" means that the polysaccharide alkali swellable rheology modifier is alkali swellable. In an aspect, the polysaccharide alkali swellable rheology modifier comprises a polysaccharide portion and a synthetic portion obtained from an anionic ethylenically unsaturated monomer, a hydrophobic ethylenically unsaturated monomer and, optionally, an associative monomer. When the associative monomer is used the resulting polymer is defined as a "polysaccharide hydrophobically modified alkali swellable rheology modifier". Polysaccharide alkali swellable rheology modifiers contain a polysaccharide portion modified by select synthetic monomers where the resulting product delivers rheology modification to aqueous systems.

For purposes of the present invention, "polysaccharide alkali swellable rheology modifier composition" means that the polysaccharide alkali swellable rheology modifier composition comprises a polysaccharide alkali swellable rheology modifier comprising of polysaccharide portion and a synthetic portion obtained from an anionic ethylenically unsaturated monomer, a hydrophobic ethylenically unsaturated monomer and, optionally, an associative monomer, unreacted polysaccharide and water.

In an embodiment, the invention relates to a polysaccharide alkali swellable rheology modifier and its use in personal care, fabric and cleaning, oil field, agricultural, paint and coating and other industrial applications. The personal care applications include, but are not limited to, formulations for hair styling gels, skin creams, sun tan lotions, moisturizers, tooth pastes, medical and first aid ointments, cosmetic ointments, suppositories, cleansers, lipstick, mascara, hair dye, cream rinse, shampoos, body soap and deodorants.

Some non-limiting examples of industrial applications for the polymers of this invention are caulk, sealants, mortars, paints and coatings, papermaking, paper coatings, adhesives, oil field additives, grouts, soaps, detergents and fabric care applications.

Suitable polysaccharides useful in the present invention can be derived from plant, animal and microbial sources and are preferably water soluble at the temperatures at which the polymerization reaction is carried out. For purposes of this invention, the term "water soluble" means that the polysaccharide has about 0.1% or greater solubility in water at reaction temperature, preferably about 1% or greater solubility in water at reaction temperature, and more preferably about 5% or greater solubility in water at reaction temperature. The reaction temperatures can vary depending on the initiating system and the pressure that the reaction is under. In an embodiment, the reaction temperature range can be about 25 to about 150° C., in another embodiment about 30 to about 120° C., but typically the reactions are conducted in the temperature range of about 40 to about 100° C.

Examples of such polysaccharides include starch, cellulose, gums (e.g., gum arabic, guar and xanthan), alginates, pectin, chitin, chitosan, carrageenan, inulin and gellan. Starches include those derived from maize and conventional hybrids of maize, such as waxy maize and high amylose (greater than 40% amylose) maize, as well as other starches such as potato, tapioca, wheat, rice, pea, sago, oat, barley, rye, and amaranth, including conventional hybrids or genetically engineered materials. In an embodiment, the preferred polysaccharide is starch and, in an embodiment, the preferred starch is based on potato. The starches can be of the native variety or a hybrid variety produced by traditional breeding programs or by artificial gene manipulation. These hybrids include, but not limited to waxy versions (starches with little or no amylose) and high amylose cultivars. Waxy starches are typically defined as having about 5% or less amylose and sometime containing about 2% or less amylose. In an embodiment, the waxy starches have about 95% or greater amylopectin. High amylose starches are defined as having about 40% or greater amylose (with the exception of pea starch which has a high amylose content of about 27% or greater amylose). In a further embodiment, the high amylose starches have an amylose content of about 60% or greater amylose. In addition, starches which have altered chain length and branch points are included in this application. In an embodiment, the preferred polysaccharides are starches or celluloses and/or their derivatives.

In an embodiment of the invention, the polysaccharides are starches and starch derivatives, including, but not limited, to thermal and/or mechanically treated starch, oxidatively, hydrolytically or enzymatically degraded starches, and chemically modified starches. These include maltodextrins, dextrin, pyrodextrins, oxidized starches, cyclodextrins and substituted cyclodextrins and higher molecular weight starches or derivatives thereof. Starch and starch hydrolysates that are hydrogenated are preferred since they lead to low color in the final application especially those that are in the alkaline pH range. Chemical modification includes hydrolysis by the action of acids, enzymes, oxidizers or heat, esterification or etherification. The chemically modified starches, after undergoing chemical modification may be cationic, anionic, non-ionic or amphoteric or hydrophobically modified and maybe crosslinked.

In one embodiment of the invention, the polysaccharides may be pregelatinized starches and starch derivatives. The pregelatinized starches suitable for use in the present invention are those starches that have been treated with heat, moisture, or chemicals to disrupt the natural granular structure and render the starch soluble in water at below the gelatinization temperature of the native starch. For purposes of the invention, pregelatinized starches are also referred to as cold water soluble starches (CWS) and the terms are used interchangeably. For a general review of how to prepare pregelatinized starches see (Starch; Chemistry and Technology, R. L. Whistler, second edition, Academic Press, Inc. New York, 1984 pages 670-673). Additionally these products can be prepared by co-jet cooking coupled to a spray drier (see Kasica et al. U.S. Pat. No. 5,571,552). In addition to being pregelatinized, the starches of this invention can further be modified to contain anionic, cationic, non-ionic and reactive groups. Derivatives of these types are described in "Modified Starches: Properties and Uses" O. B. Wurzburg, CRC Press Boca Raton, Fla., 1986 chapters 3-9. The modified starches can be prepared in the granular form and then made CWS or can be reacted in solution to produce the polymers of this invention. However, the starches can be gelatinized or cooked in the initial part of the polymerization process to produce the polysaccharide alkali swellable rheology modifiers by heating the starch solution at about 60 to about 100° C. for a long enough time to effect gelatinization. Thus, non pregelatinized starches and starch derivatives can be used by cooking them in situ.

In an embodiment, polysaccharides suitable for use with the present invention also include cellulose and cellulose derivatives, such as carboxymethyl cellulose (CMC), hydroxethyl cellulose (HEC), carboxymethyl hydroxethyl cellulose (CMHEC), hydroxypropyl cellulose, sulfoethyl cellulose and its derivatives, ethyl hydroxyethyl cellulose (EHEC), methyl ethyl hydroxyethyl cellulose (MEHEC), and hydrophobically modified ethyl hydroxyethyl celluloses HM-EHEC some of which are available from AkzoNobel. Polysaccharides also include cellulosic derivatives including plant heteropolysaccharides commonly known as hemicelluloses which are by products of the paper and pulp industry. Hemicelluloses include xylans, glucuronoxylans, arabinoxylans, glucomannans, and xyloglucans. Xylans are the most common heteropolysaccharide and are preferred. Polysaccharides such as degradation products of cellulose such as cellobiose are suitable for preparing the polymers of this invention. In an embodiment, the preferred cellulosic materials are Carboxymethyl cellulose (CMC), hydroxethyl cellulose (HEC), carboxymethyl hydroxethyl cellulose (CM-HEC), hydroxypropyl cellulose, ethyl hydroxyethyl cellulose (EHEC), methyl ethyl hydroxyethyl cellulose (MEHEC), and hydrophobically modified ethyl hydroxy ethyl celluloses (HM-EHEC). These celluloses or their derivatives generally have high viscosity in aqueous solutions due to their high molecular weight. It is preferable that the viscosity of the cellulose solution be low enough to effectively conduct the polymerization. Lower molecular weight celluloses can be used for this purpose. Alternatively, higher molecular weight cellulose or its derivative may be used and depolymerized before or during the polymerization process. The methods to depolymerize cellulose and its derivatives are known to those of ordinary skill in the art. In an embodiment, it is preferred that the viscosity of a 1% aqueous solution of the cellulose or its derivative be less than about 5000 cps, in another embodiment preferably be less than about 1000 cps and in yet another embodiment most preferably be less than about 100 cps at 25° C.

In an embodiment, when the polysaccharide is a cellulose, it is preferred that the cellulose be water soluble. For purposes of this invention, a cellulose that is water soluble has, in an embodiment, about 0.1% or greater solubility in water at 25° C. (i.e. the lowest reaction temperature), in another embodiment preferably about 1% or greater solubility in water at 25° C., and in yet another embodiment more preferably about 5% or greater solubility in water at 25° C. Water insoluble cellulose derivatives such as viscose, rayon, cellulose acetate butyrate and others are not suitable for use in the present invention since they do not make stable emulsions when used in the polymerization process of this invention.

Other suitable polysaccharides include guar, unwashed guar gum, washed guar gum, cationic guar, carboxymethyl guar (CM guar), hydroxyethyl guar (HE guar), hydroxypropyl guar (HP guar), carboxymethylhydroxypropyl guar (CMHP guar), hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar), hydrophobically modified cationic guar (HM cationic guar), guar hydroxypropyl triammonium chloride, hydroxypropyl guar hydroxypropyl triammonium chloride. Polysaccharides may also include inulin and its derivatives, such as carboxymethyl inulin. These guars or its derivatives generally have high viscosity in aqueous solutions due to their high molecular weight. It is preferable that the viscosity of the guar solution be low enough to effectively conduct the polymerization. Lower molecular weight guars can be used for this purpose. Alternatively, higher molecular weight guar or its derivative may be used and depolymerized before or during the polymerization process. The methods to depolymerize polysacharides and its derivatives are well known to those of ordinary skill in the art. In an embodiment, it is preferred that the viscosity of a 1% aqueous solution of the guar or its derivative be less than about 5000 cps, in another embodiment preferably be less than 1000 cps and in yet another embodiment most preferably be less than 100 cps at 25° C.

In an embodiment, the minimum weight percent of the polysaccharides for use with the present invention are in the range of about 5% of the polysaccharide alkali swellable rheology modifier, preferably in the range of about 10% of the polysaccharide alkali swellable rheology modifier, and most preferably in the range of about 15% of the polysaccharide alkali swellable rheology modifier. The weight of the polysaccharide alkali swellable rheology modifier is the sum of the weight of the polysaccharide and the synthetic monomers that make up this polymer. In an embodiment, the maximum weight percent of the polysaccharide is in the range of about 90% of the polysaccharide alkali swellable rheology modifier, in another embodiment preferably in the range of about 75% of the polysaccharide alkali swellable rheology modifier, and in yet another embodiment most preferably in the range of about 60% of the polysaccharide alkali swellable rheology modifier.

In an embodiment, the weight average molecular weight of the polysaccharide is preferably about 5,000,000 or less, in another embodiment more preferably about 1,000,000 or less, and in yet another embodiment most preferably about 500,000 or less. These polysaccharides may be further depolymerized as necessary for stability of the emulsion and rheology modification performance.

The molecular weight of the water soluble polysaccharides of the present invention can be determined using gel permeation chromatography (GPC) with Viscotech Triple Detector Array using the method below:
Eluent: 0.03M NaNO3 in DMSO.
Columns: 1 Phenogel MXM 7.8 mm×300 mm GPC column from Phenomenex. 40° C.
Flow Rate: 0.8 ml/min
Detector: Viscotech TDA Model 302 Triple Detector Array
Pump/Autosampler: Agilent Model 1100
Primary Standard: Pullulan 100,000 MW from American Polymer Standards.
Sample The samples were prepared by dissolving the samples in 0.03M
Preparation: NaNO3 in DMSO at 90 C for 1 hour. Concentration was about 2.0 mg/ml.
Injection Volume: 100 µl for the standard and samples.
Software: Visocotech Omnisec Software using the universal calibration method.

When the polysaccharide is a starch, the molecular weight can be measured in terms of water fluidity. Starch water fluidity ('WF') is measured using a Thomas Rotational Shear-Type Viscometer (manufactured by Arthur H. Thomas Co., Philadelphia, Pa. 19106), standardized at 30° C. with a standard oil having a viscosity of 24.73 mPas, requiring 23.12+/−0.05 seconds for 100 revolutions. Accurate and reproducible measurements of WF are obtained by determining the time which elapses for 100 revolutions at different solids levels depending on the starch's degree of conversion (as the degree of conversion increases, WF increases and viscosity decreases). The procedure used involves slurrying the required amount of starch (e.g., 6.16 g, dry basis) in 100 ml of distilled water in a covered copper cup and heating the slurry in a boiling water bath for 30 minutes with occasional stirring. The starch dispersion is then brought to the final weight (e.g., 107 g) with distilled water. The time required for 100 revolutions of the resultant dispersion at 81-83° C. is recorded and converted to a water fluidity number using the following conversion Table 1:

TABLE 1

| Time Required for 100 Revolutions (seconds) Amount of Starch used (anhydrous, g) | | | | |
| --- | --- | --- | --- | --- |
| $6.16^a$ | $8.80^b$ | $11.44^c$ | $13.20^d$ | Water Fluidity |
| 60.0 | | | | 5 |
| 39.6 | | | | 10 |
| 29.3 | | | | 15 |
| 22.6 | | | | 20 |
| 20.2 | | | | 25 |
| | 33.4 | | | 30 |
| | 27.4 | | | 35 |
| | 22.5 | | | 40 |
| | | 32.5 | | 45 |
| | | 26.8 | | 50 |
| | | 22.0 | | 55 |
| | | | 24.2 | 60 |
| | | | 19.2 | 65 |
| | | | 15.9 | 70 |
| | | | 13.5 | 75 |
| | | | 11.5 | 80 |
| | | | 10.0 | 85 |
| | | | 9.0 | 90 |

For $a$, $b$, $c$ and $d$, final weight of each starch solution is 107, 110, 113 and 115 g, respectively.

Prior work has determined the correlation between the molecular weight of fluidity starches (measured by light scattering methods) and their WF, as shown in Table 2.

TABLE 2

| Molecular weight vs. WF for degraded corn starch | | |
| --- | --- | --- |
| Sample # | WF | Mw × $10^6$ |
| 1 | 39 | 93.5 |
| 2 | 45.2 | 75.5 |
| 3 | 66.1 | 15.4 |
| 4 | 73.0 | 6.42 |

In an embodiment, the water fluidity of the starch is preferably about 75 or higher, in another embodiment more preferably about 80 or higher, and in yet another embodiment most preferably about 85 or higher.

The polymers of this invention form emulsion compositions or aqueous emulsion paste compositions which can be used as is or dried. Stable emulsions are typically formed with lower molecular weight polysaccharides. However, the higher molecular weight polysaccharides that may form an aqueous emulsion paste may give better rheology properties. In an embodiment of this invention, the polymers do not form crosslinked gels compositions during the reaction. These crosslinked gels cannot be diluted in water and neutralized to give rheology modification to aqueous systems.

If an aqueous emulsion paste is formed, the aqueous emulsion paste can be converted to a stable emulsion by a number of post treatment processes. These include, enzyme treatment or addition of a rheology modifier that is capable of suspending the particles of the aqueous emulsion paste. In an embodiment, the particle size in these emulsions or aqueous emulsion pastes that may be substantially free of surfactants are preferably about 2000 nm or less, in another embodiment more preferably about 1000 nm or less and in yet another embodiment most preferably about 500 nm or less. In an embodiment, the residual monomer of each of the monomers in these emulsions or aqueous emulsion pastes that are substantially free of surfactants are preferably about 1000 ppm or less, in another embodiment more preferably about 500 ppm or less and in yet another embodiment most preferably about 250 ppm or less.

In an embodiment, the invention relates to a polysaccharide alkali swellable rheology modifier composition. The composition comprises a polysaccharide alkali swellable rheology modifier comprising a polysaccharide portion and a synthetic portion obtained from an anionic ethylenically unsaturated monomer and at least one nonionic ethylenically unsaturated monomer, At least one of the nonionic ethylenically unsaturated monomers is a hydrophobic ethylenically unsaturated monomer present in a high enough amount to force the polymer into an emulsion form. Optionally, the polysaccharide alkali swellable rheology modifier composition may also include an associative monomer, unreacted polysaccharide and water. This can be in the form of a stable emulsion (e.g. a stable emulsion composition) or in the form of an aqueous emulsion paste (e.g. an aqueous emulsion paste composition).

In an embodiment of the invention, the emulsion polymers are self-stabilizing and unlike regular emulsion polymers may be substantially free of surfactants, such as stabilizing surfactants, during the polymerization process. The polymers of this invention do not form solution polymers wherein the polymer is completely soluble in the solvent, water. In emulsion polymers, the polymer is in the form of particles which are stabilized (but not soluble) in water at the acidic pH of the system. In typical cases, the pH is in the range 2 to 6 and more typically in the range 2.5 to 5.5. For purposes of this invention, in an embodiment, substantially free of surfactants means that the polymers have about 0.1 wt % or less surfactant, in another embodiment, about 0.01 wt % or less surfactant by weight of the polysaccharide and monomers and in yet another embodiment no surfactant is present during the polymerization process. By polymerizing under conditions that minimize the amount of surfactants present, the chances of the monomers reacting with the polysaccharide to form the polysaccharide alkali swellable rheology modifier is increased. In an embodiment of the invention, a stabilizing surfactant may be added after the polymerization to stabilize the emulsion composition.

As used herein, the term "anionic ethylenically unsaturated monomer" means an ethylenically unsaturated monomer which is capable of developing a negative charge when the polysaccharide alkali swellable rheology modifier is in an aqueous solution. These anionic ethylenically unsaturated monomers can include, but are not limited to, acrylic acid, methacrylic acid, ethacrylic acid, α-chloro-acrylic acid, α-cyano acrylic acid, β-methyl-acrylic acid (crotonic acid), α-phenyl acrylic acid, β-acryloxy propionic acid, sorbic acid, α-chloro sorbic acid, angelic acid, cinnamic acid, p-chloro cinnamic acid, β-styryl acrylic acid (1-carboxy-4-phenyl butadiene-1,3), itaconic acid, maleic acid, citraconic acid, mesaconic acid, glutaconic acid, aconitic acid, fumaric acid, tricarboxy ethylene, muconic acid, 2-acryloxypropionic acid, 2-acrylamido-2-methyl propane sulfonic acid, vinyl sulfonic acid, sodium methallyl sulfonate, sulfonated styrene, allyloxybenzene sulfonic acid, vinyl phosphonic acid and maleic acid. Combinations of anionic ethylenically unsaturated monomers can also be used. In an embodiment of the invention, the anionic ethylenically unsaturated monomer may preferably be methacrylic acid, maleic acid, acrylic acid, itaconic acid, 2-acrylamido-2-methyl propane sulfonic acid or mixtures thereof. In an embodiment, most preferably the anionic ethylenically unsaturated monomer is methacrylic acid or acrylic acid, or combinations thereof.

As used herein, the term "nonionic ethylenically unsaturated monomer" means an ethylenically unsaturated monomer which does not introduce a charge in to the polymers of this invention. These nonionic ethylenically unsaturated monomers include, but are not limited to, acrylamide, methacrylamide, N alkyl(meth)acrylamide, N,N dialkyl(meth)acrylamide such as N,N dimethylacrylamide, hydroxyalkyl (meth)acrylates, alkyl(meth)acrylates such as methylacrylate and methylmethacrylate, vinyl morpholine, vinyl pyrrolidone, vinyl caprolactum, ethoxylated alkyl, alkaryl or aryl monomers such as methoxypolyethylene glycol (meth)acrylate, allyl glycidyl ether, allyl alcohol, glycerol (meth)acrylate, and others.

For purposes of the present invention, the term "hydrophobic ethylenically unsaturated monomer" means a monomer that is hydrophobic and results in the formation of an emulsion system when reacted with the polysaccharide and the anionic ethylenically unsaturated monomer. For purposes of this invention, a hydrophobic monomer is a nonionic ethylenically unsaturated monomer defined as any nonionic ethylenically unsaturated monomer having a water solubility of less than 3 grams per 100 mls of water at 25° C. and preferably less than 1 gram per 100 mls of water at 25° C. and most preferably less than 0.1 gram per 100 mls of water at 25° C. These hydrophobic monomers may contain linear or branched alk(en)yl, cycloalkyl, aryl, alk(en)aryl moieties. Suitable hydrophobic ethylenically unsaturated monomers include C1-C7 alkyl esters or amides of acrylic and methacrylic acid including ethyl (meth)acrylate, methyl (meth)acrylate, butyl (meth)acrylate, styrene, vinyltoluene, t-butyl styrene, isopropylstyrene, and p-chlorostyrene; vinyl acetate, vinyl butyrate, vinyl caprolate, acrylonitrile, methacrylonitrile, butadiene, isobutylene, isoprene, vinyl chloride, vinylidene chloride, tertiary butyl acrylamide, benzyl (meth)acrylate, phenyl (meth)acrylate, benzyl ethoxylate (meth)acrylate, phenyl ethoxylate (meth)acrylate, 2-ethylhexyl(meth)acrylate, 2-butyloctyl(meth)acrylate, 2-hexyldecyl(meth)acrylate, 2-octyldodecyl(meth)acrylate, 2-decyltetradecyl(meth)acrylate, 2-dodecylhexadecyl(meth)acrylate, isopropyl(meth)acrylate, isobutyl(meth)acrylate, tertiary butyl (meth)acrylate, t-octyl acrylamide, octyl acrylate, lauryl acrylate, stearyl acrylate, behenyl acrylate, 2-ethylhexyl methacrylate, octyl methacrylate, lauryl methacrylate, stearyl methacrylate, behenyl methacrylate, 2-ethylhexyl acrylamide, n-octyl acrylamide, lauryl acrylamide, stearyl acrylamide, behenyl acrylamide, propyl acrylate, butyl acrylate, pentyl acrylate, hexyl acrylate, 1-allyl naphthalene, 2-allyl naphthalene, 1-vinyl naphthalene, 2-vinyl naphthalene, monomers containing silane, silanol and siloxane functionalities. Combinations of the above hydrophobic ethylenically unsaturated monomers may also be used. Preferred are ethyl (meth)acrylate, methyl (meth)acrylate, 2-ethylhexyl acrylate, butyl (meth)acrylate, vinyl acetate, tertiary butyl acrylamide and combinations thereof. In an embodiment, ethyl acrylate, methyl acrylate, vinyl acetate, butyl acrylate and combinations thereof are preferred.

For purposes of the present invention, an associative monomer is intended to mean an ethylenically unsaturated monomer containing a hydrophobe and a spacer moiety which allows the hydrophobe to be sufficiently far away from the backbone of the polymer to form hydrophobic associations in aqueous solutions. The spacer moieties are usually ethoxylate groups but any other group that extends the hydrophobe away from the backbone of the polymer may be used. The hydrophobes with a spacer moiety include, but are not limited to, alcohol ethoxylates, alkylphenoxy ethoxylates, propoxylated/butoxylated ethoxylates, ethoxylated silicones and the like. In an embodiment, the preferred hydrophobes with spacer moieties include alcohol ethoxylates and/or alkylphenoxy ethoxylates. In another embodiment, alcohol ethoxylates containing alcohols with carbon chain lengths of 6 to 40 and 6 to 100 moles of ethoxylation are more preferred. In yet another embodiment, alcohol ethoxylates containing alcohols with carbon chain lengths of 12 to 22 and 15 to 30 moles of ethoxylation are particularly preferred. The hydrophobes may be linear or branched alk(en)yl, cycloalkyl, aryl, alk(en)aryl or an alkoxylated derivative. In an embodiment, the most preferred hydrophobes are linear or branched alcohols and amines containing 12 to 32 carbons. The associative monomer may contain an ethylenically unsaturated monomer covalently linked to the hydrophobe. In an embodiment, the ethylenically unsaturated monomer part of the associate monomer preferably is a (meth)acrylate, itaconate and/or maleate which contains ester linking groups. However, the associative monomer may also contain amide, urea, urethane, ether, alkyl, aryl and other suitable linking groups. The hydrophobe may be an alkylamine or dialkylamine ethoxylate. In an embodiment, the (meth)acrylate group is most preferred. In another embodiment, preferred associative monomers are $C_{12-32}$ $(EO)_{10-30}$ meth(acrylates) or $C_{12-32}(EO)_{10-30}$ itaconates or or $C_{12-32}(EO)_{10-30}$ maleates. These associative monomers are known to those skilled in the art and any of the known associative monomers can be used as part of this invention.

In an embodiment, the minimum weight of the anionic ethylenically unsaturated monomer is about 15 weight percent or more of the total monomer added to the polymerization process, in another embodiment preferably about 20 weight percent or more of the total monomer added to the polymerization process, and in yet another embodiment, most preferably about 30 weight percent or more of the total monomer added in to the polymerization process. In an embodiment, the maximum weight of the anionic ethylenically unsaturated monomer is about 80 weight percent or less of the total monomer added in to the polymerization process, is preferably about 70 weight percent or less of the total monomer added to the polymerization process, and in another embodiment most preferably about 60 weight percent or less of the total monomer added in to the polymerization process.

In an embodiment according to the present invention, the minimum amount of hydrophobic ethylenically unsaturated monomer required is an amount effective to form an emulsion, which may depend on the hydrophobicity of the monomer. That is, the higher the hydrophobicity the less monomer would be required to form an emulsion. In an embodiment, the minimum weight of the hydrophobic ethylenically unsaturated monomer effective to form an emulsion is about 10 weight percent or more of the total monomer added to the polymerization process, in another embodiment preferably about 25 weight percent or more of the total monomer added to the polymerization process, and in yet another embodiment most preferably about 40 weight percent or more of the total monomer added to the polymerization process. In an embodiment, the maximum weight of the hydrophobic ethylenically unsaturated monomer is about 95 weight percent or less of the total monomer added to the polymerization process, in another embodiment preferably about 90 weight percent or less of the total monomer added to the polymerization process, and in yet another embodiment most preferably about 80 weight percent or less of the total monomer added to the polymerization process.

In an embodiment, the minimum weight of the associative monomer is about 0.1 weight percent or more of the total monomer added to the polymerization process, in another embodiment preferably about 1 weight percent or more of the total monomer added to the polymerization process, and in yet another embodiment most preferably about 2 weight percent or more of the total monomer added to the polymerization process. In an embodiment, the maximum weight of the associative monomer is about 30 weight percent or less of the total monomer added to the polymerization process, in another embodiment preferably about 25 weight percent or less of the total monomer added to the polymerization process, and in yet another embodiment most preferably about 20 weight percent or less of the total monomer added in to the polymerization process.

It has been found that styrene or substituted styrene do not react well with the polymers of the invention and may lead to high residual monomer levels which cause undesirable odors. Accordingly, in an embodiment of the invention, if styrene or substituted styrene is included as one part of the hydrophobic ethylenically unsaturated monomer, then the amount of this monomer is preferably about 10 weight percent or less of the total monomer, in another embodiment more preferably about 5 weight percent or less of the total monomer and in yet another embodiment is most preferably about 1 weight percent or less of the total monomer.

In an aspect, the present invention is directed to a process for preparing the polysaccharide alkali swellable rheology modifiers. The process comprises dissolving the polysaccharide in water and heating the solution to a temperature sufficient to initiate the reaction. In an embodiment, the temperature sufficient to initiate the reaction is approximately 25 to 150° C. and in another embodiment preferably 30° C. to 95° C. In an embodiment, the polysaccharide maybe depolymerized before or during the polymerization step to a molecular weight that is sufficient to provide a stable emulsion in the end product. In an embodiment, the depolymerization may be accomplished by using free radicals or enzymes or any other process known to those of ordinary skill in the art. In a typical process according to the present invention, a mixture of monomers and an aqueous solution of an initiator are added over a period of time. In an embodiment, the monomer may be methacrylic acid mixed with a hydrophobic monomer, such as ethyl acrylate. Optionally, an associative monomer maybe added to the monomer mix. After the polymerization is completed, the reaction mixture is then cooked for a period of time sufficient to lower the residual monomer. Additional initiator to scavenge any remaining monomer may then be added. The temperature required depends on the initiating system used and would be known to one skilled in the art. The residual level of each monomer is less than about 1000 ppm of the emulsion polymer composition, more preferably less than about 500 ppm of the emulsion polymer composition, and most preferably less than about 100 ppm of the emulsion polymer composition.

In an embodiment, chain transfer agents and crosslinking agents may be added during the polymerization process. Suitable chain transfer agents include, but are not limited to, mercaptans, such as, for example, dodecylmercaptan, methyl mercaptopropionate, and 3-mercaptopropionic acid, 2-mercaptoethanol, combinations thereof and the like.

Suitable crosslinking agents include, but are not limited to, polyethylenically unsaturated copolymerizable monomers that typically have 2 or more double bonds which are effective for crosslinking, such as, for example, diallylphthalate, divinylbenzene, vinyl crotonate, allyl methacrylate, trimethylol propane triacrylate, ethylene glycol diacrylate or dimethacrylate, polyethylene glycol diacrylate or dimethacrylate, 1,6-hexanediol diacrylate or dimethacrylate, diallyl benzene, combinations thereof, and the like.

The resulting reaction product may be in one or more forms. In an embodiment, the reaction product may be in the form of a stable emulsion composition containing water, the polymers of the invention and any unreacted polysaccharide which is a liquid and then ready to use by diluting to the necessary concentration and adding a neutralization agent. In another embodiment, the reaction product may be in the form of an aqueous emulsion paste composition that contains water. For purposes of this invention, an "aqueous emulsion paste composition" is defined as an emulsion containing water, the polymers of the invention and any unreacted polysaccharide that does not flow like a liquid, but instead has solid like flow properties. Once the paste is formed and separated from the reaction product, the aqueous emulsion paste is stable as a solid containing water with in an embodiment about 10 weight % or more, in another embodiment preferably about 15 weight % or more and in yet another embodiment most preferably about 20 weight % or more solids, and the emulsion does not phase separate for approximately 1 month at 25° C. In another embodiment, the emulsion does not separate for approximately 6 months at 25° C. This aqueous emulsion paste maybe used as is, but for ease of handling, the aqueous emulsion paste composition may be dried and the dried product may be used. In a further embodiment, a stabilizing agent may be added to the aqueous emulsion paste composition (post polymerization) to form a stable emulsion composition which then can be used. This stabilizing agent may be a synthetic or a naturally derived polymeric thickener or gelling additive. Some examples of such materials include, but are not limited to, pectin, alginate, xanthan gum, guar, cellulosics and chemically or physically modified derivatives of these natural polymeric thickeners, such as carboxymethyl cellulose, hydroxyethyl cellulose, hydroxyethyl ethylcellulose, hydroxypropyl cellulose, oxidized cellulose and dehydroxanthan gum. In an embodiment, the preferred stabilizing agent is guar, xanthan or a cellulose derivative, such as ethyl hydroxyethyl cellulose (EHEC). In an embodiment, the stabilizing agent is about 1 weight percent or more of the polymer of the emulsion paste composition but can be as high as about 5 to about 20 weight percent of the polymer of the emulsion paste composition.

For purposes of this invention, a stable emulsion system is defined as comprising the polymers of this invention, unreacted polysaccharide and water, in liquid form, with at about 10 weight % or more and preferably about 15 weight % or more and most preferably about 20 weight % or more solids, and in an embodiment the emulsion does not phase separate for approximately 1 month at 25° C. and in another embodiment preferably does not separate for approximately 6 months at 25° C.

The stable emulsion composition or the aqueous emulsion paste composition may be diluted with water and then neutralized to give viscosity and rheology to the aqueous systems. In one embodiment of the invention, the stable emulsion composition or the aqueous emulsion paste composition is readily dilutable. For purposes of this invention, "readily dilutable" means that the emulsion composition or the aqueous emulsion paste composition can be diluted to about a 1-5 weight %, aqueous polymer solution or dispersion by adding water using stirring and adding a neutralizing agent and heating, if necessary, and more preferably diluted to about a 1-5 weight % aqueous polymer solution or dispersion by adding water and using stirring. After the neutralization agent is added and the pH raised, in an embodiment a pH in the range from about 5 to about 12, in another embodiment from about 5 to about 10 and yet another embodiment from about 7 to about 10, the polymer is dissolved in water and forms a solution, i.e. it is no longer in the dispersed or emulsion phase. This is evidenced by a visual change of a white emulsion to a clear solution. In an embodiment of the invention, the stable emulsion composition or the aqueous emulsion paste composition, when diluted to about 2% solids and neutralized to a pH of about 8 with suitable neutralizing agents, generates a viscosity at 25° C. of about 500 cps or more, in another embodiment preferably about 2500 cps or more and in another embodiment more preferably about 5000 cps or more at 10 rpm when measured using a Brookfield viscometer.

In an embodiment, the polysaccharide alkali swellable rheology modifier or polysaccharide hydrophobically modified alkali swellable rheology modifiers include emulsion compositions or aqueous emulsion paste compositions in the pH range about 2 to about 6. Consequently, these compositions need to be activated by neutralizing with a neutralizing agent. Suitable neutralizing agents which may be included in the composition of the present invention include, but are not limited to, alkyl monoamines containing from about 2 to about 22 carbon atoms, such as triethylamine, stearylamine and laurylamine, and amino alcohols such as triethanolamine, 2-amino-2-methyl-1,3-propanediol and 2-amino-2-methyl-1-propanol, and inorganic neutralizing agents, such as sodium hydroxide and potassium hydroxide. Other combinations of useful neutralizing agents are described in U.S. Pat. No. 4,874,604 to Sramek, which is incorporated by reference in its entirety herein. In an embodiment, the neutralizing agents may be used alone or in combination. In an embodiment, the polysaccharide alkali swellable rheology modifier or polysaccharide hydrophobically modified alkali swellable rheology modifiers are neutralized by a base. The neutralizing agent may be present in an amount effective to neutralize a percentage of the polymer's free acid groups and render the polymer water-soluble or water-dispersible. In one embodiment, the neutralizing agent may be present in an amount sufficient to neutralize the free acid groups of the polymer from about 8 percent to about 100 percent neutralization of the total free acid groups of the polymer. In another embodiment, the free acid groups of the polymer may be neutralized from about 25 percent to about 100 percent. In another embodiment, the free acid groups of the polymer may be neutralized from about 50 percent to about 100 percent. In yet another embodiment, the free acid groups of the polymer will be neutralized from about 70 percent to about 100 percent. In still yet another embodiment, the free acid groups of the polymer may be neutralized from about 80 to about 100 percent. The base may also be used in excess of 100 percent neutralization to increase the solution pH. In another embodiment, when the final pH range of the aqueous system is desired to be about 5 to about 7, the solution containing the polymers of this invention may be neutralized to the pH of about 7 to about 9 and then the pH adjusted back to about 5 to about 7 using a suitable acid.

As used herein, the initiating system is any free radical initiating system. In an embodiment, the initiating system is water soluble. Suitable initiators include, but are not limited to, peroxides, azo initiators as well as redox systems, such as tert-butyl hydroperoxide and erythorbic acid, and metal ion based initiating systems. Initiators may also include both inorganic and organic peroxides. In an embodiment, the inorganic peroxides, such as sodium persulfate, potassium persulfate and ammonium persulfate, are preferred. In a further embodiment, the metal ion based initiating systems including Fe and hydrogen peroxide, as well as Fe in combination with other peroxides, are preferred. Azo initiators, especially water soluble azo initiators, may also be used. Water soluble azo initiators include, but are not limited to, 2,2'-Azobis[2-(2-imidazolin-2-yl)propane]dihydrochloride, 2,2'-Azobis[2-(2-imidazolin-2-yl)propane]disulfate dihydrate, 2,2'-Azobis(2-methylpropionamidine)dihydrochloride, 2,2'-Azobis[N-(2-carboxyethyl)-2-methylpropionamidine]hydrate, 2,2'-Azobis {2-[1-(2-hydroxyethyl)-2-imidazolin-2-yl]propane}dihydrochloride, 2,2'-Azobis[2-(2-imidazolin-2-yl)propane], 2,2'-Azobis(1-imino-1-pyrrolidino-2-ethylpropane)dihydrochloride, 2,2'-Azobis {2-methyl-N-[1,1-bis(hydroxymethyl)-2-hydroxyethl]propionamide}, 2,2'-Azobis[2-methyl-N-(2-hydroxyethyl)propionamide] and others. The initiators when added before the monomer can be used to depolymerize the polysaccharide to a desired molecular weight. Furthermore, a different initiating system could be used during the polymerization process. Finally, a third initiating system can be used to scavenge the residual monomer. All 3 of these initiating systems can be same of different. Thus, it is contemplated that in an embodiment of the invention, combinations of the initiating systems can also be used.

If persulfate is used in combination with undegraded starch, the persulfate initiator is preferably about 1 weight percent or less of the total weight of the undegraded starch and monomer, and preferably about 0.5 weight percent or less of the total weight of the undegraded starch and monomer and most preferably about 0.1 weight percent or less of the total weight of the undegraded starch and monomer.

In an embodiment, the invention relates to a polysaccharide alkali swellable rheology modifier and its use in personal care, fabric and cleaning, oil field, agricultural, adhesive, asphalt emulsions, paint and coatings and other industrial applications. In an embodiment, the polymers of this invention may be added to these formulations at least about 0.1% polymer by weight of the formulation, more preferably at least about 0.5% polymer by weight of the formulation and most preferably at least about 1.0% polymer by weight of the formulation. In an embodiment, the polymers of this invention may be added to these formulations at most about 20% polymer by weight of the formulation, more preferably at most about 15% polymer by weight of the formulation and most preferably at least about 10% polymer by weight of the formulation.

The polymers of this invention can be used in aqueous protective coating compositions. These polymers increase and maintain the viscosity at required levels under specific processing conditions and end-use situations. In particular, the polymers of this invention are useful in all kinds of coatings such as decorative and protective coatings and in paper coatings. The polymers of this invention can be used as rheology modifiers for water-based protective coating compositions. Water-based protective coating compositions are commonly known as latex paints or dispersion paints and have been known for a considerable number of years. The adjustment of the rheology properties of such an aqueous protective coating composition is challenging, since the coating composition needs not only to provide good leveling and excellent sag resistance, but rather the coating compositions should also have an ICI viscosity which is neither too low nor too high in order to allow an easy application.

In agricultural formulations, the polymers of this invention provide drift control of agricultural sprays, reducing carryover to other areas and permitting more efficient spray directly on foliage. The fabric and cleaning applications include use of these polymers in liquid detergents. These detergent formulations are known in the art and include, liquids for fabric cleaning, hard surface cleaners, hand dishwash and automatic dishwash.

In oil field applications, the polymers of this invention may be used in fracturing operations. For these applications, it is desired to use liquid compositions with viscoelastic properties. Such compositions, for instance, may be used to stimulate oil wells wherein impeded flow paths lead to an insufficient hydrocarbon production, a technique known as (hydraulic) fracturing and the specialized fluids used in said technique are referred to as fracturing fluids. For such a fracturing process, the compositions are typically injected via the wellbore into the formation at sufficient pressures to create fractures in the formation rocks, thus creating channels through which the hydrocarbons may more readily flow into the wellbore. In an embodiment, the fracturing fluids should impart a minimal pressure drop in the pipe within the wellbore during placement and have an adequate viscosity to carry proppant (sand) material that prevents the fracture from closing. Moreover, the fracturing fluids should have a minimal leak-off rate to avoid fluid migration into the formation rocks so that, notably, the fracture can be created and propagated and should degrade so as not to leave residual material that may prevent accurate hydrocarbons to flow into the wellbore.

The personal care applications include, but are not limited to, formulations for hair styling gels, skin creams, sun tan lotions, moisturizers, tooth pastes, medical and first aid ointments, cosmetic ointments, suppositories, cleansers, lipstick, mascara, hair dye, cream rinse, shampoos, body soap and deodorants, hair care and styling formulations, shave prep and hand sanitizers including alcohol based hand sanitizers.

Suitable personal care applications also include formulation for use on the skin, eyelashes or eyebrows, including, without limitation, cosmetic compositions such as mascara, facial foundations, eyeliners, lipsticks, and color products; skin care compositions such as moisturizing lotions and creams, skin treatment products, skin protection products in the form of an emulsion, liquid, stick, or a gel; sun care compositions such as sunscreens, sunscreen emulsions, lotions, creams, sunscreen emulsion sprays, liquid/alcohol sunscreen sprays, sunscreen aqueous gels, broad spectrum sunscreens with UVA and UVB actives, sunscreens with organic and inorganic actives, sunscreens with combinations of organic and inorganic actives, suntan products, self-tanning products, and after sun products etc. Particularly suitable compositions are personal care emulsions, more particularly suitable are sun care compositions such as sunscreen emulsions and sunscreen emulsion sprays. The personal care composition may be in any form, including without limitation in sprays, emulsions, lotions, gels, liquids, sticks, waxes, pastes, powders, and creams.

The personal care compositions may also include other optional components commonly used in the industry, and these will vary greatly depending upon the type of composition and the functionality and properties desired. Without limitation, these components include thickeners, suspending agents, emulsifiers, UV filters, sunscreen actives, humectants, moisturizers, emollients, oils, waxes, solvents, chelating agents, vitamins, antioxidants, botanical extracts, silicones, neutralizing agents, preservatives, fragrances, dyes, pigments, conditioners, polymers, antiperspirant active ingredients, antiacne agents, anti-dandruff actives, surfactants, exfoliants, film formers, propellants, tanning accelerator, hair fixatives and colors. The polymers of the present invention are compatible with most other components used in conventional personal care compositions. For example, sunscreen compositions may contain at least one component selected from the group comprising organic UV filters, inorganic UV actives, UVA and/or UVB suncreen actives, octinoxate, octisalate, oxybenzone, homosalate, octocrylene, avobenzene, titanium dioxide, starch, conditioning agents, emulsifiers, other rheology modifiers and thickeners, neutralizers, emollients, solvents, film formers, moisturizers, antioxidants, vitamins, chelating agents, preservatives, fragrances, and zinc oxide. Skin care and cosmetic compositions may contain at least one component selected from the group consisting of vitamins, anti-aging agents, moisturizers, emollients, emulsifiers, surfactants, preservatives, pigments, dyes, colors and insect repellents.

When used in personal care formulations, such as hair care and styling formulations, for example styling gels, optional additional ingredients can be added to provide a variety of further additional properties. Various other additives, such as active and functional ingredients, may be included in the personal care formulation as defined herein. These include, but are not limited to, emollients, humectants, thickening agents, electrolytes and salts surfactants, UV light inhibitors, fixative polymers preservatives pigments dyes, colorants, alpha hydroxy acids, aesthetic enhancers such as starch perfumes and fragrances, film formers (water proofing agents) antiseptics, antifungal, antimicrobial and other medicaments and solvents. Additionally, conditioning agents can be used in combination with the polymers of this invention, for example, cationic guar gum, cationic hydroxyethyl cellulose, cationic synthetic polymers and cationic fatty amine derivatives. These blended materials help to provide more substantivity and effective conditioning properties in hair. The electrolytes and salts are particularly useful in boosting the viscosity of the shampoo and improving its suspending properties.

Some non-limiting examples of polymers that can used in conjunction with the polymers of this invention are polyoxythylenated vinyl acetate/crotonic acid copolymers, vinyl acetate crotonic acid (90/10) copolymers, vinyl acetate/crotonic acid/vinyl neodecanoate terpolymers, N-octylacrylamide/methylacrylate/hydroxypropyl methacrylate/acrylic acid/tert-butylaminoethyl methacrylate copolymers, and methyl vinyl ether/maleic anhydride (50/50) copolymers monoesterified with butanol or ethanol, acrylic acid/ethyl acrylate/N-tert-butyl-acrylamide terpolymers, and poly (methacrylic acid/acrylamidomethyl propane sulfonic acid), acrylates copolymer, octylacrylamide/acrylates/butylaminoethyl methacrylate copolymer, acrylates/octylacrylamide copolymer, VA/crotonates/vinyl Neodeanoate copolymer, poly(N-vinyl acetamide), poly(N-vinyl formamide), corn starch modified, sodium polystyrene sulfonate, polyquaterniums such as polyquaternium-4, polyquaternium-7, polyquaternium-10, polyquaternium-11, polyquartemium-16, polyquaternium-28, polyquaternium-29, polyquaternium-46, polyether-1, polyurethanes, VA/acrylates/lauryl methacrylate copolymer, adipic acid/dimethylaminohydroxypropyl diethylene AMP/acrylates copolymer, methacrylol ethyl betaine/acrylates copolymer, PVP/dimethylaminoethylmethacrylate copolymer, PVP/DMAPA acrylates copolymer, PVP/vinylcaprolactam/DMAPA acrylates copolymer, vinyl caprolactam/PVP/dimethylaminoethyl methacrylate copolymer, VA/butyl maleate/isobomyl acrylate copolymer, VA/crotonates copolymer, acrylate/acrylamide copolymer, VA/crotonates/vinyl propionate copolymer, vinylpyrrolidone/vinyl acetate/vinyl propionate terpolymers, VA/crotonates, cationic and amphoteric guar, polyvinylpyrrolidone (PVP), polyvinylpyrrolidone/vinyl acetate copolymer, PVP acrylates copolymer, vinyl acetate/crotonic acid/vinyl prionate, acrylates/acrylamide, acrylates/octylacrylamide, acrylates/hydroxyacrylates copolymer, and alkyl esters of polyvinylmethylether/maleic anhydride, diglycol/cyclohexanedimethanol/isophthalates/sulfoisophthalates copolymer, vinyl acetate/butyl maleate and isobornyl acrylate copolymer, vinylcaprolactam/PVP/dimethylaminoethyl methacrylate, vinyl acetate/alkylmaleate half ester/N-substituted acrylamide terpolymers, vinyl caprolactam/vinylpyrrolidone/methacryloamidopropyl trimethylammonium chloride terpolymer methacrylates/acrylates copolymer/amine salt, polyvinylcaprolactam, polyurethanes, hydroxypropyl guar, hydroxypropyl guar hydroxypropyl trimmonium chloride, poly (methacrylic acid/acrylamidomethyl propane sulfonic acid, poylurethane/acrylate copolymers and hydroxypropyl trimmonium chloride guar, particularly acrylates copolymer, octylacrylamide/acrylates/butylaminoethyl methacrylate copolymer, acrylates/octylacrylamide copolymer, VA/crotonates/vinyl Neodeanoate copolymer, poly(N-vinyl acetamide), poly(N-vinyl formamide), polyurethane, corn starch modified, sodium polystyrene sulfonate, polyquaternium-4, polyquartemium-10, and polyurethane/acrylates copolymer.

In addition to the polymers of this invention, the personal care compositions of the invention may also include a cosmetically acceptable ingredient. The ingredient can be a emollient, fragrance. exfoliant, medicament, whitening agent, acne treatment agent, a preservative, vitamins, proteins, a cleanser or conditioning agent.

Examples of cleansers suitable for use the present invention include, but are not limited to, are sodium lauryl sulfate (SLS), sodium laureth sulfate (SLES), ammonium lauryl ether sulfate (ALES), alkanolamides, alkylaryl sulfonates, alkylaryl sulfonic acids, alkylbenzenes, a e acetates, amine oxides, amines, sulfonated amines and amides, betaines, block polymers, carboxylated alcohol or alkylphenol ethoxylates, diphenyl sulfonate derivatives, ethoxylated alcohols, ethoxylated alkylphenols, ethoxylated amines and/or amides, ethoxylated fatty acids, ethoxylated fatty esters and oils, fatty esters (other than glycol, glycerol, etc.), fluorocarbon-based surfactants, glycerol esters, glycol esters, heterocyclics, imidazolines and imidazoline derivatives, isethionates, lanolin-based derivatives, lecithin and lecithin derivatives, lignin and lignin derivatives, methyl esters, monoglycerides and derivatives, olefin sulfonates, phosphate esters, phosphorous organic derivatives, polymeric (polysaccharides, acrylic acid, acrylamide), propoxylated and ethoxylated fatty acids, propoxylated and ethoxylated fatty alcohols, propoxylated and ethoxylated alkyl phenols, protein-based surfactants, quaternary surfactants, sarcosine derivatives, silicone-based surfactants, soaps, sorbitan derivative, sucrose and glucose esters and derivatives, sulfates and sulfonates of oils and fatty acids, sulfates and sulfonates ethoxylated alkyl phenols, sulfates of alcohols, sulfates of ethoxylated alcohols, sulfates of fatty esters, sulfonates of benzene, cumene, toluene and xylene, sulfonates of condensed naphthalenes, sulfonates of dodecyl and tridecyl benzenes, sulfonates of naphthalene and alkyl naphthalene, sulfonates of petroleum, sulfosuccinamates, sulfosuccinates and derivatives.

Preservatives are often used in personal care formulations to provide long term shelf stability. These can be selected from among methylparaben, propylparaben, butylparaben, DMDM hydantoin, imidazolidinyl urea, gluteraldehyde, phenoxyethanol, benzalkonium chloride, methane ammonium chloride, benzethonium chloride, benzyl alcohol, chlorobenzyl alcohol, methylchloroisothiazolinone, methylisothiazolinone, sodium benzoate, chloracetamide, triclosan, iodopropynyl butylcarbamate, sodium pyrithione, and zinc pyrithione.

In an embodiment of this invention, particularly where the hair formulation is a shampoo, the formulation contains a sulfate free surfactant and the polymers of this invention. Examples of sulfate free surfactants include, but are not limited to, ethoxylated alkylphenols, ethoxylated amines and/or amides, ethoxylated fatty acids, ethoxylated fatty esters and oils, fatty esters (other than glycol, glycerol, etc.), fluorocarbon-based surfactants, glycerol esters, glycol esters, heterocyclics, imidazolines and imidazoline derivatives, isethionates, lanolin-based derivatives, lecithin and lecithin derivatives, lignin and lignin derivatives, methyl esters, monoglycerides and derivatives, phosphate esters, phosphorous organic derivatives, polymeric (polysaccharides, acrylic acid, acrylamide), propoxylated and ethoxylated fatty acids, propoxylated and ethoxylated fatty alcohols, propoxylated and ethoxylated alkyl phenols, protein-based surfactants, quaternary surfactants, sarcosine derivatives, siliconebased surfactants, alpha-olefin sulfonate, alkylaryl sulfonates, sulfonates of oils and fatty acids, sulfonates of ethoxylated alkyl phenols, sulfonates of benzene, cumene, toluene and xylene, sulfonates of condensed naphthalenes, sulfonates of dodecyl and tridecyl benzenes, sulfonates of naphthalene and alkyl naphthalene, sulfonates of petroleum and derivatives thereof. In an embodiment of the invention, the sulfate free surfactants are sulfonates or ethoxylates.

In another embodiment the formulation contains sulfated surfactants. Some non-limiting examples of sulfated surfactants are sodium lauryl sulfate (SLS), sodium laureth sulfate (SLES), alkanolamides, alkylaryl sulfonic acids, sulfates of oils and fatty acids, sulfates of ethoxylated alkyl phenols, sulfates of alcohols, sulfates of ethoxylated alcohols, sulfates of fatty esters, sulfosuccinamates, sulfosuccinates and derivatives thereof.

In addition to the polymer(s) of this invention, shampoo compositions may optionally include other ingredients. Some non-limiting examples of these ingredients include, but are not limited to, conditioning agents such as silicone oils, either volatile or non-volatile, natural and synthetic oils. Suitable silicone oils that can be added to the compositions include dimethicone, dimethiconol, polydimethylsiloxane, silicone oils with various DC fluid ranges from Dow Corning. Suitable natural oils, such as olive oil, almond oil, avocado oil, wheatgerm oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate can also be used. Some examples of non-ionic conditioning agents are polyols such as glycerin, glycol and derivatives, polyethyleneglycols, which may be known by the trade names Carbowax® PEG from Union Carbide and Polyox® WSR range from Amerchol, polyglycerin, polyethyleneglycol mono- or di-fatty acid esters.

Suitable cationic polymers that may be used in the formulation are those of best known with their CTFA category name Polyquaternium. Some examples of this class of polymer are Polyquaternium 6, Polyquaternium 7, Polyquaternium 10, Polyquaternium 11, Polyquaternium 16, Polyquaternium 22 and Polyquaternium 28, Polyquaternium 4, Polyquaternium 37, Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

Naturally derived cellulose type polymers known as Polymer JR® type from Amerchol, Polyquaternium 10 or cationic guar gum known with trade name Jaguar® from Rhone-Poulenc, and Guar hydroxypropyl trimonium chloride, chitosan and chitin can also be included in the personal care formulations as cationic natural polymers may also optionally be included with the inventive polymers.

The polymers of this invention can also be used in liquid detergent compositions that include one or more surfactants, such as those selected from anionic, nonionic, cationic, amphoteric, and zwitterionic surfactants. In an embodiment, the preferred surfactants are suitable for use in isotropic liquid detergent compositions and are mixtures of anionic and nonionic surfactants although it is to be understood that any surfactant may be used alone or in combination with any other surfactant or surfactants. These liquid detergent systems as well as the surfactants used in them are described in U.S. Pat. No. 6,462,013 which is incorporated herein by reference in its entirety.

The polymers of this invention may also be used in liquid detergent compositions and may further optionally comprise at least one additive. Suitable additives may include, for example, builders, dispersants, polymers, ion exchangers, alkalies, anticorrosion materials, antiredeposition materials, antistatic agents, optical brighteners, perfumes, fragrances, dyes, fillers, oils, chelating agents, enzymes, fabric whiteners, brighteners, sudsing control agents, solvents, hydrotropes, bleaching agents, bleach precursors, buffering agents, soil removal agents, soil release agents, fabric softening agents, and opacifiers. In general, such additives and their amounts are known to those skilled in the art.

The present invention will now be illustrated by the following examples. The examples are intended to exemplify the present invention but are not intended to limit the scope of the invention in any way. The breadth and scope of the invention are to be limited solely by the claims appended hereto.

EXAMPLES

Measurement of Zero Shear Viscosity

SR-5000 Rheometer (from Rheometrics) was used to measure zero-shear viscosity. Sample was loaded between two 40-mm parallel plates, and the gap of the plate was adjusted to 1.5 mm. Temperature of the sample was control by a peltier. Steady Stress Sweep test was conducted with the following parameters at 25° C. and 45° C.

Sweep Mode=Log
Initial Stress=0.1 Pa
Final Stress=1000.0 Pa
Points Per Decade=10
Max Time Per Data Point=10 s The flow curve is obtained by plotting viscosity versus shear rate, as shown in FIG. 1. Typically, the flow curve has a "flat" plateau region of viscosity at low shear rate, followed by a shear-thinning region. Zero-shear viscosity is calculated by taking the average of the viscosity values of the data points in the "flat" plateau region at low shear rate as shown in FIG. 1.

Example 1

80 grams of a low molecular weight ethyl hydroxyethyl cellulose (EHEC) Bermocoll® E230 from AkzoNobel (weight average molecular weight of approximately 300,000) was dispersed in 1675 grams of water containing 1.6 grams of sodium sulfate in a 2 liter reactor equipped with stirrer and a heating mantle. The mixture was heated to 85° C. while sparging with nitrogen. 0.356 grams of ferrous ammonium sulfate hexahydrate dissolved in 21 grams of water and 8.3 grams of 35% hydrogen peroxide dissolved in 53 grams of water was added. This was then held under nitrogen at 85° C. for 15 minutes to depolymerize the ethyl hydroxyethyl cellulose. A monomer feed containing 97.2 grams of methacrylic acid, 120 grams of ethyl acrylate, 0.2 grams of diallyl phthalate and 21.43 grams of $C_{18}$ alcohol with 20EO itaconate (associative monomer) was then added over 45 minutes. Concurrently, an initiator solution containing 6.7 grams of 35% hydrogen peroxide dissolved in 42.8 grams of water was added over 110 minutes. A nitrogen sparge is continued during these additions. The reaction mixture was then cooked at 90° C. for an hour. The solution was cooled down to 75° C. and 0.42 g of 70% tert butyl hydroperoxide in 2.06 g of water was added in one shot. A solution of 0.18 grams of erythorbic acid dissolved in 13.72 grams of water was added over 1 hour and then the reaction was held at 70° C. for 30 minutes. The reaction product was allowed to cool overnight and separates out in to an aqueous top phase and a bottom phase that is an opaque white paste which we term the aqueous emulsion paste composition. This aqueous emulsion paste composition had 24.3% polymer with the rest being water. The polymer portion of this aqueous paste was diluted to 2% and neutralized to pH 7 by slow addition of 50% NaOH. The result solution formed a gel which had a viscosity of 95,300 cps at 0.5 rpm as measured by a Brookfield viscometer. The polymer composition of the aqueous emulsion paste composition remained a paste for 3 months and longer and was easily redispersed in water on dilution.

Example 2

Stabilization to Form a Stable Emulsion System

To stabilize the paste as a pourable liquid, the aqueous emulsion paste of Example 1 can be diluted to 20% polymer with water. Under high shear, guar gum was added as a stabilizer to a total 0.3% of the solution. The stabilizer was 1.5 weight % of the polysaccharide hydrophobically modified alkali swellable rheology modifier in this emulsion composition. The resulting product is a stable emulsion composition that is liquid and pourable.

Example 3

Stabilization to Form a Stable Emulsion System

To stabilize the paste as a pourable liquid, the aqueous emulsion paste of Example 1 can be diluted to 20% polymer with water. Under high shear, Bermocoll® M 800× (EHEC) from AkzoNobel was added as a stabilizer to a total 0.3% of the solution. The stabilizer was 1.5 weight % of the polysaccharide hydrophobically modified alkali swellable rheology modifier in this emulsion composition. The resulting product is a stable emulsion composition that is liquid and pourable.

Example 4

Stabilization to Form a Stable Emulsion System

To stabilize the paste as a pourable liquid, the aqueous emulsion paste of Example 1 can be diluted to 20% polymer with water. Under high shear, xanthan gum was added as a stabilizer to a total 5% of the solution. The stabilizer was 33 weight % of the polysaccharide hydrophobically modified alkali swellable rheology modifier in this emulsion composition. The resulting product is a stable emulsion composition that is liquid and pourable.

Example 5

Evaluation of Sample of Example 1 in Personal Care Applications (Shampoo)

200 grams of typical shampoo base was prepared at room temperature by adding 59.58 grams of Deionized water to a 250 ml beaker. A small 1½ inch jiffy mixer blade was inserted into the beaker and attached to an overhead mixer. The batch was allowed to mix with a vortex extending to the middle of the beaker. Then 24.30 grams (3% active polymer) of Example 1was added and allowed to mix until uniform. This was followed by adding 62.74 grams of Sodium Laureth Sulfate (25.2% active Standapol ES-2 from Cognis Corporation, FairField, N.J.). This was allowed to mix until it was homogenous. Then 27.58 grams of Sodium Lauryl sulfate (Witconate WAC LA, Akzo Nobel, Houston, Tex.) was added and mixed until homogenous. Then 22.80 grams of Cocamidoproply Betaine (Crodateric CAB 30, Croda Inc, Edison, N.J.) was added an allowed to mix until homogenous. Then 1.0 grams of DMDM Hydantoin and Iodopropynyl Butylcarbamate Glydant Plus (Liquid), Lonza Corp Allendale, N.J.) was added and the batch was mixed until homogenous. The pH was then adjusted to 6.5+/−0.25 using 25% sodium hydroxide (Fisher Scientific, Fairlawn, N.J.) as needed. Once the batch was uniform 2 grams of cosmetic beads, Floraspheres JoJoba MDS beads (Floratech, Chandler, Ariz.) were gently folded into the batch until they were evenly distributed throughout the batch.

| Sample of Example 1 (3.0% Active Solids) | | | |
|---|---|---|---|
| pH | Viscosity* | Rheology | 45° C. Suspension Results |
| 6.34 | 21,300 | Quick Flow | Passed 8+ weeks to date |

*RVTD Viscometer with Spindle C @ 10 rpm, measure in centipoise (cps.)
The zero shear viscosity of this shampoo was measured to be 1680 Pa-s at 25° C.

To test the suspension properties of the cosmetic beads in this batch it was placed in a 45° C. oven and the dispersion of the beads was visually monitored for migration of the beads. Any sample that showed migration of the beads was deemed a failure. This batch was tested at the 3.0% active level and had a nice shampoo-like viscosity. The beads stayed suspended in the sample over an 8 week period at 45° C., as shown in the top photograph of FIG. 2.

Example 6

Base Shampoo without Example 1 Polymer Composition 200 grams of typical shampoo base was prepared by adding 83.88 grams of Deionized water to a 250 ml beaker. A small 1½ inch jiffy mixer blade was inserted into the beaker and attached to an overhead mixer. The batch was allowed to mix with a vortex extending to the middle of the beaker. This was followed by adding 62.74 grams of Sodium Laureth Sulfate (25.2% active Standapol ES-2 from Cognis Corporation, FairField, N.J.). This was allowed to mix until it was homogenous. Then 27.58 grams of Sodium Lauryl sulfate (Witconate WAC LA, Akzo Nobel, Houston, Tex.) was added and mixed until homogenous. Then 22.80 grams of Cocamidoproply Betaine (Crodateric CAB 30, Croda Inc, Edison, N.J.) was added an allowed to mix until homogenous. Then 1.0 grams of DMDM Hydantoin and IodopropynylButylcarbamate Glydant Plus (Liquid), Lonza Corp Allendale, N.J.) was added and the batch was mixed until homogenous. The pH was then adjusted to 6.5+/−0.25 using 25% sodium hydroxide (Fisher Scientific, Fairlawn, N.J.) as needed. Once the batch was uniform 2 grams of cosmetic beads, Florashperes JoJoba MDS beads (Floratech, Chandler, Ariz.) were gently folded into the batch until they were evenly distributed throughout the batch.

NOTE: The base shampoo without the Sample from Example 1 was also tested for suspension properties to validate that the base system alone would or would not suspend the cosmetic beads. The results are as follows:

| Initial pH | Viscosity | Rheology | RT** Suspension Results |
|---|---|---|---|
| 6.51 | 4,000 | Quick Flow | Failed - beads migrated after a 2 hour period |

Figure 2:
FIG. 2 is a comparison of two photographs showing a base shampoo sample prepared with the polymer according to Example 1 compared to the same base shampoo sample but without the polymer according to Example 1.
Figure 2:
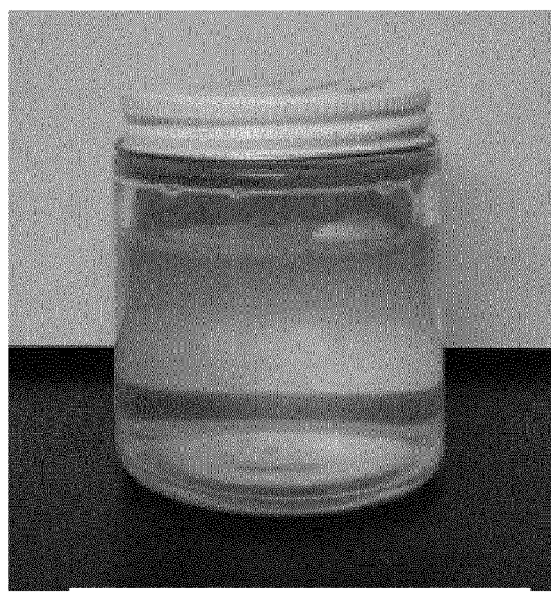

The base system showed a thin, low viscosity and did not exhibit any suspension qualities with the beads migrating to the top of the sample after a 2 hour period, as shown in the bottom photograph of FIG. 2. This proved that the base system needs a suspending agent to have the ability to suspend the cosmetic beads.

Example 7

80 grams of a maltodextrin C*DRY MD 01955 (DE 5 from Cargill, weight average molecular weight in the range 2 to 10,000) was dissolved in 1100 grams of water in a 2 liter reactor equipped with stirrer and a heating mantle. The mixture was heated to 85 C while sparging with nitrogen for 1 hour. 0.356 grams of ferrous ammonium sulfate hexahydrate dissolved in 21 grams of water and 8.3 grams of 35% hydrogen peroxide dissolved in 53 grams of water was added. This was then held under nitrogen at 85° C. for 15 minutes. A monomer feed containing 97.2 grams of methacrylic acid, 120 grams of ethyl acrylate, 0.2 grams of diallyl phthalate and 21.43 grams of $C_{18}$ alcohol with 20EO itaconate (associative monomer) was then added over 45 minutes. Concurrently, an initiator solution containing 6.7 grams of 35% hydrogen peroxide dissolved in 42.8 grams of water was added over 110 minutes. A nitrogen sparge is continued during these additions. The reaction mixture was then cooked at 90° C. for an hour. The final product was a stable emulsion composition with 18.8% solids and the emulsion was stable for 3 months and longer. The residual methacrylic acid was 12 ppm and the residual level of ethyl acrylate was undetectable.

Example 8a using Sample from Example 7 in hair gels

The polymer of Example 7 was used in a hair gel and then tested using the formula below (Table 3):

TABLE 3

| Raw Material | % w/w |
|---|---|
| Deionized Water | 86.89 |
| Polymer of Example 7 | 10.64 |
| Sodium Hydroxide (10%) | 2.17 |
| Preservative | 0.30 |

*pH adjusted to 6.50

Procedure:
1. Add Water to container with mixing, using a standard propeller blade.
2. Add Polymer of Example 7 to container with mixing.
3. Add Sodium Hydroxide slowly to container to reach desired pH. Adjust mixing speed as necessary to maintain good turnover.
4. Once uniform and clear, add Preservative to container.

Results for Concentration Testing and Clarity

Gels were created using 2-4% active thickening polymer at a pH of 6.5-8 (Table 3). Thickening was observed to begin at a pH of 6.3 and continued to thicken until approximately 7.0. Clarity was observed to increase as the polymer is neutralized and once finished was under 10 NTU for all samples, as illustrated in Table 4. This shows equivalent performance when compared to a 0.4% Carbomer 980 (rheology modifier from Lubrizol) gel with a value of 5.85 NTU, using the formula in the Table 3.

TABLE 4

| Concentration (active) | pH | Clarity (NTU) |
|---|---|---|
| 2 | 6.5 | 7.37 |
| 3 | 6.5 | 6.00 |
| 4 | 6.5 | 4.81 |
| 2 | 7.0 | 3.84 |
| 3 | 7.0 | 2.81 |
| 4 | 7.0 | 2.80 |
| 2 | 8.0 | 3.63 |
| 3 | 8.0 | 3.22 |
| 4 | 8.0 | 3.34 |

Example 8b

Polymer of Example 7 in Another Hair Gel Formulation

The following formula was used to create 2 different Hair Gels one with the polymer of Example 7 and the other with Carbomer 980 (Table 5):

TABLE 5

| Raw Material | % w/w |
| --- | --- |
| Deionized Water | 76.63 |
| Polymer 7 | 18.62 |
| PVP K-90 | 3.0 |
| Aminomethyl Propanol | 1.25 |
| Euxyl PE9010 | 0.50 |

*pH adjusted to ~7.0

Procedure:
1. Add Water to container with mixing using a standard propeller blade.
2. Add Polymer of Example 7 (or Carbomer 980) to container. Mix well until dispersed fully.
3. Add Aminomethyl Propanol to desired pH; continue to mix well.
4. Add PVP K-90 (from Ashland) to container. Mix well until dissolved.
5. Add Euxyl PE 9010 (from Schuelke and Mayr). Mix well; gel will be clear.

These 2 hair gels were evaluated for viscosity using the same method previously used in Example 8a except spindle TC @ 10 rpm was utilized. The results are shown in Table 6.

TABLE 6

| Sample | Viscosity (cps) | pH |
| --- | --- | --- |
| Polymer of Example 7 | 68100 | 7.06 |
| Carbomer 980 | 69100 | 6.65 |

Results for Subjective Testing

Hair Gels that were created above were used for subjective evaluations.

The following method was used to perform subjective testing:

10" long, ¼" wide, 4.50 g net, European brown hair was wet with water and gently combed through to remove tangles. 0.50 g of hair gel was applied to the swatch and was spread throughout the swatch using a top-to-bottom motion and rotating the swatch for even application. Samples were dried in a 50° C. oven for 1 hour and panelists tested for the following qualities: Gloss, Stiffness, Dry Comb, Flake, and Anti-Static properties. Dry Feel was omitted from this test for safety purposes due to possible monomer residuals. A total of 8 sets (16 swatches) were evaluated using a standard Ace black comb for combing tests.

It was seen that no statistical differences were seen for any test category between the gels made with the Polymer of Example 7 and the gels made with Carbomer 980. Both the gels had similar performance (Table 7).

TABLE 7

| Gel made with the Polymer of Example 7 vs. Gel made with Carbomer 980 (from Lubrizol) | | | | |
| --- | --- | --- | --- | --- |
| Gloss | Stiffness | Dry Comb | Flake | AntiStat |
| = | = | = | = | = |

Example 9

63 grams of a maltodextrin C*DRY MD 01955 (DE 5 from Cargill) was dissolved in 467 grams of water in a 1 liter reactor equipped with stirrer and a heating mantle. The mixture was heated to 85° C. while sparging with nitrogen for 1 hour. 0.192 grams of ferrous ammonium sulfate hexahydrate dissolved in 21 grams of water and 8.3 grams of 35% hydrogen peroxide dissolved in 53 grams of water was added. This was then held under nitrogen at 85° C. for 15 minutes. A monomer feed containing 92.2 grams of methacrylic acid, 67.7 grams of ethyl acrylate, 20.7 grams of methyl methacrylate and 7.5 grams of $C_{16}$ alcohol with 20 EO itaconate (associative monomer) was then added over 45 minutes. Concurrently, an initiator solution containing 6.7 grams of 35% hydrogen peroxide dissolved in 42.8 grams of water was added over 110 minutes. The clear solution started to look like an opaque white emulsion 10 minutes in to the feed. A nitrogen sparge is continued during these additions. The reaction mixture was then cooked at 90° C. for an hour. The final product was a stable emulsion composition with 28.1% solids and the emulsion was stable for 3 months and longer. The starch was 25 weight percent of the total polymer.

Example 10

91 grams of a maltodextrin C*DRY MD 01955 (DE 5 from Cargill) was dissolved in 663 grams of water in a 1 liter reactor equipped with stirrer and a heating mantle. The mixture was heated to 85° C. while sparging with nitrogen for 1 hour. A monomer solution containing 120 grams of methacrylic acid, 89.47 grams of ethyl acrylate, 27.1 grams of methyl methacrylate and 9.4 grams of $C_{16}$ alcohol with 20EO itaconate (associative monomer) was prepared. 5 weight percent of this monomer mixture was added to the reactor. At the same time 0.27 grams of ammonium persulfate dissolved in 28.4 grams of water was added. The reaction mixture was held at 85° C. for 15 minutes under N2. The rest of the monomer was then added over 90 minutes. Concurrently, an initiator solution containing 0.12 grams of ammonium persulfate dissolved in 45 grams of water was added over 120 minutes. The clear solution started to look like an opaque white emulsion 30 minutes in to the feed. A nitrogen sparge is continued during these additions. The reaction mixture was then cooked at 85 C for an hour. A solution of 0.18 grams of ammonium persulfate dissolved in 48 grams of water was added over 1 hour and then the reaction was held at 85° C. for 30 minutes. The final product was a stable emulsion composition with 30% solids and the emulsion was stable for 3 months and longer.

Example 11

91 grams of a maltodextrin C*DRY MD 01955 (DE 5 from Cargill) was dissolved in 663 grams of water in a 1 liter reactor equipped with stirrer and a heating mantle. The mixture was heated to 85° C. while sparging with nitrogen for 1 hour. A monomer solution containing 120 grams of methacrylic acid, 89.47 grams of ethyl acrylate, 27.1 grams of methyl methacrylate, 0.23 grams of diallyl phthalate and 9.4 grams of $C_{16}$ alcohol with 20EO itaconate (associative monomer) was prepared. 5 weight percent of this monomer mixture was added to the reactor. At the same time 0.27 grams of ammonium persulfate dissolved in 28.4 grams of water was added. The reaction mixture was held at 85° C. for 15 minutes under N2. The rest of the monomer was then added over 90 minutes. Concurrently, an initiator solution containing 0.12 grams of ammonium persulfate dissolved in 45 grams of water was added over 120 minutes. The clear solution started to look like an opaque white emulsion 30 minutes in to the feed. A nitrogen sparge is continued during these additions. The reaction mixture was then cooked at 85 C for an hour. A solution of 0.18 grams of ammonium persulfate dissolved in 48 grams of water was added over 1 hour and then the reaction was held at 85° C. for 30 minutes. The final product was a stable emulsion composition with 30% solids and the emulsion was stable for 3 months and longer.

Example 12

The polymers of the Examples 7, 9, 10 and 11 were diluted to the levels shown in Table 8. They were then neutralized to pH 8 using 10% NaOH. The viscosity of these solutions at different rpms was measured using a Brookfield viscometer. These data indicate that these polymers are good alkali swellable rheology modifiers.

TABLE 8

| Polymer of Example | % Solids | Polymer dosage | Viscosity (cps) @ different rpms | | | | |
|---|---|---|---|---|---|---|---|
| | | | 0.5 | 5 | 10 | 20 | 50 |
| 7 | 18.8 | 1 | 4000 | 1280 | 880 | 620 | 380 |
| | | 2 | 120000 | 21600 | 13700 | 8350 | 4920 |
| 9 | 28.1 | 5 | 32000 | 14000 | 10700 | 8000 | 5060 |
| 10 | 29.6 | 1 | 2000 | 680 | 520 | 410 | 324 |
| | | 2 | 3600 | 2800 | 2380 | 1960 | 1432 |
| | | 4 | 28000 | 19400 | 15200 | 11050 | 6940 |
| 11 | 29.7 | 1 | 800 | 360 | 280 | 230 | 200 |
| | | 2 | 31600 | 7480 | 4980 | 3380 | 2136 |
| | | 4 | 158000 | 31200 | 18800 | 12250 | 7080 |

Example 13

91 grams of a 85% Perfectamyl A4692 (oxidized potato starch from Avebe with a weight average molecular weight of 510,000) was dissolved in 706 grams of water in a 1 liter reactor equipped with stirrer and a heating mantle. The mixture was heated to 85° C. while sparging with nitrogen for one hour. A monomer solution containing 101.7 grams of methacrylic acid, 125.9 grams of ethyl acrylate, 0.24 grams of diallyl phthalate and 22.4 grams of $C_{18}$ alcohol with 20EO itaconate (associative monomer) was prepared. 5 weight percent of this monomer mixture was added to the reactor. At the same time 0.27 grams of ammonium persulfate dissolved in 19.8 grams of water was added. The reaction mixture was held at 85° C. for 15 minutes under N2. The rest of the monomer was then added over 90 minutes. Concurrently, an initiator solution containing 0.17 grams of ammonium persulfate dissolved in 45 grams of water was added over 120 minutes. A nitrogen sparge was continued during these additions. The reaction mixture was then cooked at 85° C. for an hour. A solution of 0.17 grams of ammonium persulfate dissolved in 48 grams of water was added over 1 hour and then the reaction was held at 85° C. for 30 minutes. The final product was an emulsion composition with 29% solids and pH 4.3 with an average particle size in the range 1600-1900 nm. The emulsion changed in to an aqueous emulsion paste composition with a week. The residual ethylacrylate content was 242 ppm of the solution.

The aqueous emulsion paste composition was diluted to 2% solids and then neutralized to pH 7.5 using 10% NaOH. This formed a gel that suspended beads for at least one week at 45° C.

Example 14

91 grams of C*DRY MD 01955 (DE 5 from Cargill) was dissolved in 706 grams of water in a 1 liter reactor equipped with stirrer and a heating mantle. The mixture was heated to 85° C. while sparging with nitrogen for one hour. A monomer solution containing 101.7 grams of methacrylic acid, 125.9 grams of ethyl acrylate, 0.29 grams of trimethylolpropane triacrylate and 22.4 grams of $C_{18}$ alcohol with 20EO itaconate (associative monomer) was prepared. 5 weight percent of this monomer mixture was added to the reactor. At the same time 0.27 grams of ammonium persulfate dissolved in 19.8 grams of water was added. The reaction mixture was held at 85° C. for 15 minutes under N2. The rest of the monomer was then added over 90 minutes. Concurrently, an initiator solution containing 0.17 grams of ammonium persulfate dissolved in 45 grams of water was added over 120 minutes. A nitrogen sparge was continued during these additions. The reaction mixture was then cooked at 85° C. for an hour. A solution of 0.17 grams of ammonium persulfate dissolved in 48 grams of water was added over 1 hour and then the reaction was held at 85° C. for 30 minutes. The final product was a stable emulsion composition with 28% solids with an average particle size in the range 300 nm and was stable for at least a month at 25° C.

Example 15

177 grams of C*DRY MD 01955 (DE 5 from Cargill) was dissolved in 706 grams of water in a 1 liter reactor equipped with stirrer and a heating mantle. The mixture was heated to 85° C. while sparging with nitrogen for one hour. A monomer solution containing 69.3 grams of methacrylic acid, 85.7 grams of ethyl acrylate, 0.16 grams of diallyl phthalate and 15.3 grams of $C_{18}$ alcohol with 20EO itaconate (associative monomer) was prepared. 5 weight percent of this monomer mixture was added to the reactor. At the same time 0.18 grams of ammonium persulfate dissolved in 19.8 grams of water was added. The reaction mixture was held at 85° C. for 15 minutes under N2. The rest of the monomer was then added over 90 minutes. Concurrently, an initiator solution containing 0.12 grams of ammonium persulfate dissolved in 45 grams of water was added over 120 minutes. A nitrogen sparge was continued during these additions. The reaction mixture was then cooked at 85° C. for an hour. A solution of 0.11 grams of ammonium persulfate dissolved in 48 grams of water was added over 1 hour and then the reaction was held at 85° C. for 30 minutes. The final product was a stable emulsion composition with 29% solids with an average particle size in the range 200 nm. The polysaccharide was approximately 50 weight percent of the combined weight of the polysaccharide and the monomers.

Example 16

89.5 grams of a 94% Stackote 8 (depolymerized dent starch from Ingredion with a weight average molecular weight of 600,000) was dissolved in 646 grams of water in a 1 liter reactor equipped with stirrer and a heating mantle. The mixture was heated to 85° C. while sparging with nitrogen for one hour. A monomer solution containing 93.1 grams of methacrylic acid, 115.2 grams of ethyl acrylate, 0.22 grams of diallyl phthalate and 20.5 grams of $C_{18}$ alcohol with 20 EO itaconate (associative monomer) was prepared. 5 weight percent of this monomer mixture was added to the reactor. At the same time 0.25 grams of ammonium persulfate dissolved in 18.1 grams of water was added. The reaction mixture was held at 85° C. for 15 minutes under N2. The rest of the monomer was then added over 90 minutes. Concurrently, an initiator solution containing 0.17 grams of ammonium persulfate dissolved in 42 grams of water was added over 120 minutes. A nitrogen sparge was continued during these additions. The reaction mixture was then cooked at 85° C. for an hour. A solution of 0.15 grams of ammonium persulfate dissolved in 7 grams of water was added over 0.5 hours and then the reaction was held at 85° C. for 30 minutes. The final product was an emulsion composition with 22% solids with an average particle size of around 160 nm.

Example 17

111.4 grams of a 83% Perfectamyl LV (oxidized potato starch from Avebe with a weight average molecular weight of 240,000) was dissolved in 706 grams of water in a 1 liter reactor equipped with stirrer and a heating mantle. The mixture was heated to 85 C while sparging with nitrogen for one hour. A monomer solution containing 101.7 grams of methacrylic acid, 125.9 grams of ethyl acrylate, 0.24 grams of diallyl phthalate and 22.4 grams of $C_{18}$ alcohol with 20 EO itaconate (associative monomer) was prepared. 5 weight percent of this monomer mixture was added to the reactor. At the same time 0.27 grams of ammonium persulfate dissolved in 19.8 grams of water was added. The reaction mixture was held at 85° C. for 15 minutes under N2. The rest of the monomer was then added over 90 minutes. Concurrently, an initiator solution containing 0.17 grams of ammonium persulfate dissolved in 45 grams of water was added over 120 minutes. A nitrogen sparge was continued during these additions. The reaction mixture was then cooked at 85° C. for an hour. A solution of 0.16 grams of ammonium persulfate dissolved in 7 grams of water was added over 15 minutes and then the reaction was held at 85° C. for 30 minutes. The final product was an emulsion composition with 29% solids with an average particle size in the range 860 nm. The emulsion composition changed to a stable aqueous emulsion paste composition within a week.

Example 18

91 grams of C*DRY MD 01955 (DE 5 from Cargill) was dissolved in 706 grams of water in a 1 liter reactor equipped with stirrer and a heating mantle. The mixture was heated to 85° C. while sparging with nitrogen for one hour. A monomer solution containing 101.7 grams of methacrylic acid, 125.9 grams of ethyl acrylate, 0.24 grams of diallyl phthalate and 22.4 grams of $C_{18}$ alcohol with 20EO itaconate (associative monomer) was prepared. 5 weight percent of this monomer mixture was added to the reactor. At the same time 0.18 grams of ammonium persulfate dissolved in 19.8 grams of water was added. The reaction mixture was held at 85° C. for 15 minutes under N2. The rest of the monomer was then added over 90 minutes. Concurrently, an initiator solution containing 0.17 grams of ammonium persulfate dissolved in 45 grams of water was added over 120 minutes. A nitrogen sparge was continued during these additions. The reaction mixture was then cooked at 85° C. for an hour. A solution of 0.16 grams of ammonium persulfate dissolved in 7 grams of water was added over 10 minutes and then the reaction was held at 85° C. for 30 minutes. The final product was a stable emulsion composition with 29% solids and a pH of 3.2 with an average particle size in the range 500 nm. The residual ethyl acrylate level was 121 ppm.

Example 19

103 grams of Thermflo (lightly crosslinked waxy maize starch from Ingredion) was dissolved in 956 grams of water in a 1 liter reactor equipped with stirrer and a heating mantle. The mixture was heated to 95° C. while sparging with nitrogen for one hour. 10 grams of 35% hydrogen peroxide was added and held at 95° C. for 3 hours. The reaction was then cooled to 85° C. A monomer solution containing 101.7 grams of methacrylic acid, 125.9 grams of ethyl acrylate, 0.24 grams of diallyl phthalate and 22.4 grams of $C_{18}$ alcohol with 20 EO itaconate (associative monomer) was prepared. 5 weight percent of this monomer mixture was added to the reactor. At the same time 0.27 grams of ammonium persulfate dissolved in 19.8 grams of water was added. The reaction mixture was held at 85° C. for 15 minutes under N2. The rest of the monomer was then added over 90 minutes. Concurrently, an initiator solution containing 0.17 grams of ammonium persulfate dissolved in 45 grams of water was added over 120 minutes. A nitrogen sparge was continued during these additions. The reaction mixture was then cooked at 85° C. for an hour. A solution of 0.16 grams of ammonium persulfate dissolved in 7 grams of water was added over 10 minutes and then the reaction was held at 85° C. for 30 minutes. The final product was a stable emulsion composition with 21.7% solids and a pH of 2.8 with an average particle size in the range 400 nm.

Example 20

56.0 grams of low molecular weight ethyl hydroxyethyl cellulose (EHEC) Bermocoll® E230 from AkzoNobel was dissolved in 837.5 grams of water containing 1.12 grams of sodium sulfate in a 1 liter reactor equipped with stirrer and a heating mantle. The mixture was heated to 85° C. while sparging with nitrogen. 0.1781 grams of ferrous ammonium sulfate hexahydrate dissolved in 10.57 grams of water and 4.15 grams of 35% hydrogen peroxide dissolved in 26.51 grams of water was added. This was then held under nitrogen at 85° C. for 15 mins to depolymerize the ethyl hydroxyethyl cellulose. A monomer feed containing 42.27 grams of methacrylic acid, 52.32 grams of ethyl acrylate, 0.10 grams of diallyl phthalate and 9.32 grams of $C_{18}$ alcohol with 20 EO itaconate (associative monomer) was then added over 45 minutes. The EHEC was 35 weight percent of the total weight of the EHEC and monomer. Concurrently, an initiator solution containing 3.35 grams of 35% hydrogen peroxide dissolved in 21.42 grams of water was added. A nitrogen sparge is continued during these additions. The reaction mixture was then cooked at 90° C. for an hour. The reaction product was allowed to cool overnight and separates out in to an aqueous top phase and a bottom phase that is an opaque white paste which was the aqueous emulsion paste composition. This aqueous emulsion paste composition weighed approximately 700 grams and had 18.05% polymer with the rest being water. The polymer portion of this aqueous emulsion paste composition was diluted to 2% and neutralized to pH 8 by slow addition of 10% NaOH. The result solution formed a gel which had a viscosity of 33,600 cps at 0.5 rpm. The polymer of the aqueous emulsion paste composition remained a paste for 3 months and longer and was easily redispersed in water on dilution.

Example 21

42.11 grams of an 85% Perfectamyl A4692 (oxidized potato starch from Avebe with a weight average molecular weight of 510,000) was dissolved in 837.5 grams of water in a 1 liter reactor equipped with stirrer and a heating mantle. The mixture was heated to 85° C. while sparging with nitrogen. 0.1781 grams of ferrous ammonium sulfate hexahydrate dissolved in 10.57 grams of water and 4.15 grams of 35% hydrogen peroxide dissolved in 26.51 grams of water was added. This was then held under nitrogen at 85° C. for 15 mins to depolymerize the potato starch. A monomer feed containing 48.62 grams of methacrylic acid, 60.17 grams of ethyl acrylate, 0.12 grams of diallyl phthalate and 10.72 grams of $C_{18}$ methylamine with 20 EO itaconate (associative monomer) was then added over 45 minutes. Concurrently, an initiator solution containing 3.35 grams of 35% hydrogen peroxide dissolved in 21.42 grams of water was added. A nitrogen sparge is continued during these additions. The reaction mixture was then cooked at 90° C. for an hour. The solution was cooled down to 75° C. and 0.42 g of 70% tert butyl hydroperoxide in 2.06 g of water was added in one shot. A solution of 0.18 grams of erythorbic acid dissolved in 13.72 grams of water was added over 1 hour and then the reaction was held at 70° C. for 30 minutes. The final product was a stable emulsion composition with 14.0% solids. The solution was diluted to 3% and neutralized to pH 8 by slow addition of 10% NaOH. The result solution formed a gel which had a viscosity of 350,000 cps at 0.5 rpm.

Example 22

42.11 grams of an 85% Perfectamyl A4692 (oxidized potato starch from Avebe with a weight average molecular weight of 510,000) was dissolved in 832.14 grams of water in a 1 liter reactor equipped with stirrer and a heating mantle. The mixture was heated to 85° C. while sparging with nitrogen. 0.1781 grams of ferrous ammonium sulfate hexahydrate dissolved in 10.57 grams of water and 4.15 grams of 35% hydrogen peroxide dissolved in 26.51 grams of water was added. This was then held under nitrogen at 85° C. for 15 mins to depolymerize the potato starch. A monomer feed containing 43.26 grams of methacrylic acid, 60.17 grams of ethyl acrylate, 0.12 grams of diallyl phthalate and 21.43 grams of a urethane associate monomer (3-isopropenyl-α,α-dimethylbenzyl isocyanate reacted with alcohol ethoxylate (C18 with 25 moles of ethoxylate) to form the corresponding urethane monomer) was then added over 45 minutes. Concurrently, an initiator solution containing 3.35 grams of 35% hydrogen peroxide dissolved in 21.42 grams of water was added. A nitrogen sparge is continued during these additions. The reaction mixture was then cooked at 90° C. for an hour. The solution was cooled down to 75° C. and 0.42 g of 70% tert butyl hydroperoxide in 2.06 g of water was added. A solution of 0.18 grams of erythorbic acid dissolved in 13.72 grams of water was added over 1 hour and then the reaction was held at 70° C. for 30 minutes. The final product was a stable emulsion with 13.1% solids. The solution was diluted to 3% and neutralized to pH 8 by slow addition of 10% NaOH. The result solution formed a gel which had a viscosity of 218,000 cps at 0.5 rpm.

Example 23

58.95 grams of an 85% Perfectamyl A4692 (oxidized potato starch from Avebe with a weight average molecular weight of 510,000) was dissolved in 575.44 grams of water in a 1 liter reactor equipped with stirrer and a heating mantle. The mixture was heated to 85° C. while sparging with nitrogen. 0.2494 grams of ferrous ammonium sulfate hexahydrate dissolved in 7.00 grams of water and 5.81 grams of 35% hydrogen peroxide dissolved in 14.00 grams of water was added. This was then held under nitrogen at 85° C. for 15 mins to depolymerize the potato starch. A monomer feed containing 60.56 grams of methacrylic acid, 84.24 grams of ethyl acrylate, 0.16 grams of diallyl phthalate and 30.00 grams of CD 559 associative monomer mixture (50% $C_{16-18}$ alcohol with 20EO, 25% methacrylic acid and 25% water) was then added over 45 minutes. Concurrently, an initiator solution containing 4.69 grams of 35% hydrogen peroxide dissolved in 29.98 grams of water was added. A nitrogen sparge is continued during these additions. The reaction mixture was then cooked at 90° C. for an hour. The solution was cooled down to 75° C. and 0.58 of 70% tert butyl hydroperoxide in 2.88 g of water was added. A solution of 0.25 grams of erythorbic acid dissolved in 19.21 grams of water was added over 1 hour and then the reaction was held at 70° C. for 30 minutes. The final product was a stable emulsion composition with 24.3% solids. The solution was diluted to 3% and neutralized to pH 8 by slow addition of 10% NaOH. The result solution formed a gel which had a viscosity of 158,000 cps at 0.5 rpm.

Example 24

66.53 grams of an 85% Perfectamyl A4692 (oxidized potato starch from Avebe with a weight average molecular weight of 510,000) was dissolved in 649.38 grams of water in a 1 liter reactor equipped with stirrer and a heating mantle. The mixture was heated to 85° C. while sparging with nitrogen. 0.2814 grams of ferrous ammonium sulfate hexahydrate dissolved in 7.90 grams of water and 6.55 grams of 35% hydrogen peroxide dissolved in 15.80 grams of water was added. This was then held under nitrogen at 85° C. for 5 mins to depolymerize the potato starch. A monomer feed containing 76.81 grams of methacrylic acid, 95.07 grams of ethyl acrylate, 0.18 grams of diallyl phthalate and 33.86 grams of CD 559 associative monomer mixture (50% $C_{16-18}$ alcohol with 20 EO, 25% methacrylic acid and 25% water) was then added over 45 minutes. Concurrently, an initiator solution containing 5.29 grams of 35% hydrogen peroxide dissolved in 33.84 grams of water was added. A nitrogen sparge is continued during these additions. The reaction mixture was then cooked at 90° C. for an hour. The solution was cooled down to 75° C. and 0.66 of 70% tert butyl hydroperoxide in 3.25 g of water was added. A solution of 0.29 grams of erythorbic acid dissolved in 21.68 grams of water was added over 1 hour and then the reaction was held at 70° C. for 30 minutes. The final product was a stable emulsion composition with 19.4% solids. The solution was diluted to 3% and neutralized to pH 8 by slow addition of 10% NaOH. The result solution formed a gel which had a viscosity of 318,000 cps at 0.5 rpm.

Example 25

66.53 grams of an 85% Perfectamyl A4692 (oxidized potato starch from Avebe with a weight average molecular weight of 510,000) was dissolved in 649.38 grams of water in a 1 liter reactor equipped with stirrer and a heating mantle. The mixture was heated to 85° C. while sparging with nitrogen. 0.2814 grams of ferrous ammonium sulfate hexahydrate dissolved in 7.90 grams of water and 6.55 grams of 35% hydrogen peroxide dissolved in 15.80 grams of water was added. This was then held under nitrogen at 85° C. for 10 mins to depolymerize the potato starch. A monomer feed containing 76.81 grams of methacrylic acid, 95.07 grams of ethyl acrylate, 0.18 grams of diallyl phthalate and 33.86 grams of CD 559 associative monomer mixture (50% $C_{16-18}$ alcohol with 20 EO, 25% methacrylic acid and 25% water) was then added over 45 minutes. Concurrently, an initiator solution containing 5.29 grams of 35% hydrogen peroxide dissolved in 33.84 grams of water was added. A nitrogen sparge is continued during these additions. The reaction mixture was then cooked at 90° C. for an hour. The solution was cooled down to 75° C. and 0.66 of 70% tert butyl hydroperoxide in 3.25 g of water was added. A solution of 0.29 grams of erythorbic acid dissolved in 21.68 grams of water was added over 1 hour and then the reaction was held at 70° C. for 30 minutes. The final product was a stable emulsion composition with 24.1% solids. The solution was diluted to 3% and neutralized to pH 8 by slow addition of 10% NaOH. The result solution formed a gel which had a viscosity of 280,000 cps at 0.5 rpm.

Example 26

66.53 grams of an 85% Perfectamyl A4692 (oxidized potato starch from Avebe with a weight average molecular weight of 510,000) was dissolved in 649.38 grams of water in a 1 liter reactor equipped with stirrer and a heating mantle. The mixture was heated to 85° C. while sparging with nitrogen. 0.2814 grams of ferrous ammonium sulfate hexahydrate dissolved in 7.90 grams of water and 6.55 grams of 35% hydrogen peroxide dissolved in 15.80 grams of water was added. Immediately, a monomer feed containing 76.81 grams of methacrylic acid, 95.07 grams of ethyl acrylate, 0.18 grams of diallyl phthalate and 33.86 grams of CD 559 associative monomer mixture (50% $C_{16-18}$ alcohol with 20EO, 25% methacrylic acid and 25% water) was then added over 45 minutes. Concurrently, an initiator solution containing 5.29 grams of 35% hydrogen peroxide dissolved in 33.84 grams of water was added. A nitrogen sparge is continued during these additions. The reaction mixture was then cooked at 90° C. for an hour. The solution was cooled down to 75° C. and 0.66 of 70% tert butyl hydroperoxide in 3.25 g of water was added. A solution of 0.29 grams of erythorbic acid dissolved in 21.68 grams of water was added over 1 hour and then the reaction was held at 70° C. for 30 minutes. The final product was a stable emulsion with 23.8% solids. The solution was diluted to 3% and neutralized to pH 8 by slow addition of 10% NaOH. The result solution formed a gel which had a viscosity of 284,000 cps at 0.5 rpm.

Example 27

26.97 grams of a Kleptose, a beta cyclodextrin from Roquette, was dissolved in 837.5 grams of water in a 1 liter reactor equipped with stirrer and a heating mantle. The mixture was heated to 85° C. while sparging with nitrogen. A monomer feed containing 55.14 grams of methacrylic acid, 68.25 grams of ethyl acrylate, 0.13 grams of diallyl phthalate and 12.15 grams of $C_{18}$ alcohol with 20EO itaconate (associative monomer) was then added over 45 minutes. Concurrently, an initiator solution containing 0.22 grams of ammonium persulfate dissolved in 21.42 grams of water was added. A nitrogen sparge is continued during these additions. The reaction mixture was then cooked at 90° C. for an hour. The solution was cooled down to 75° C. and 0.42 g of 70% tert butyl hydroperoxide in 2.06 g of water was added. A solution of 0.18 grams of erythorbic acid dissolved in 13.72 grams of water was added over 1 hour and then the reaction was held at 70° C. for 30 minutes. The final product was a stable emulsion with 13.7% solids. The solution was diluted to 3% and neutralized to pH 8 by slow addition of 10% NaOH.

Example 28

48 grams of low molecular weight ethyl hydroxyethyl cellulose (EHEC) Bermocoll® E230 from AkzoNobel was dispersed in 837.5 grams of water containing 0.96 grams of sodium sulfate in a 1 liter reactor equipped with stirrer and a heating mantle. The mixture was heated to 85° C. while sparging with nitrogen. 0.1781 grams of ferrous ammonium sulfate hexahydrate dissolved in 10.57 grams of water and 4.15 grams of 35% hydrogen peroxide dissolved in 26.51 grams of water was added. This was then held under nitrogen at 85° C. for 15 minutes to depolymerize the ethyl hydroxyethyl cellulose. A monomer feed containing 45.52 grams of methacrylic acid, 56.34 grams of ethyl acrylate, 0.11 grams of diallyl phthalate and 10.03 grams of C18 alcohol with 20 EO itaconate (associative monomer) was then added over 45 minutes. Concurrently, an initiator solution containing 3.35 grams of 35% hydrogen peroxide dissolved in 21.42 grams of water was added over 60 minutes. A nitrogen sparge is continued during these additions. The reaction mixture was then cooked at 90° C. for an hour. The reaction product was allowed to cool overnight and separates out in to an aqueous top phase and a bottom phase that is an opaque white paste which we term the aqueous emulsion paste. This aqueous emulsion paste phase had 21.8% polymer with the rest being water. The polymer portion of this aqueous paste was diluted to 2% and neutralized to pH 7 by slow addition of 10% NaOH. The result solution formed a gel which had a viscosity of 20,000 cps at 0.5 rpm as measured by a Brookfield viscometer. The polymer of the aqueous emulsion paste remained a paste for 3 months and longer and was easily redispersed in water on dilution.

Example 29

104.0 grams of low molecular weight ethyl hydroxyethyl cellulose (EHEC) Bermocoll® E230 from AkzoNobel was dispersed in 837.5 grams of water containing 1.12 grams of sodium sulfate in a 1 liter reactor equipped with stirrer and a heating mantle. The mixture was heated to 85° C. while sparging with nitrogen. 0.1781 grams of ferrous ammonium sulfate hexahydrate dissolved in 10.57 grams of water and 4.15 grams of 35% hydrogen peroxide dissolved in 26.51 grams of water was added. This was then held under nitrogen at 85° C. for 15 minutes to depolymerize the ethyl hydroxyethyl cellulose. A monomer feed containing 22.76 grams of methacrylic acid, 28.17 grams of ethyl acrylate, 0.05 grams of diallyl phthalate and 5.02 grams of C18 alcohol with 20 EO itaconate (associative monomer) was then added over 30 minutes. The polysaccharide content was approximately 65 weight percent of the polysaccharide and monomer. Concurrently, an initiator solution containing 3.35 grams of 35% hydrogen peroxide dissolved in 21.42 grams of water was added over 50 minutes. A nitrogen sparge is continued during these additions. The reaction mixture was then cooked at 90° C. for an hour. The final product was a single phase, very viscous liquid with 13.14% solids. The solution was diluted to 2% and neutralized to pH 8 by slow addition of 10% NaOH. The result solution formed a gel which had a viscosity of 7,840 cps at 0.5 rpm as measured by a Brookfield viscometer. The polymer of the aqueous emulsion paste remained a paste for 3 months and longer and was easily redispersed in water on dilution.

Example 30

59 grams of low molecular weight ethyl hydroxyethyl cellulose (EHEC) Bermocoll® E230 from AkzoNobel was dispersed in 676.81 grams of water containing 2.71 grams of sodium sulfate in a 1 liter reactor equipped with stirrer and a heating mantle. The mixture was heated to 85° C. while sparging with nitrogen. A monomer mixture containing 59.69 grams of dimethyl aminoethyl methacrylate, 96.11 grams of ethyl acrylate and 8.22 grams of C16 alcohol with 20 EO itaconate (associative monomer) was prepared and mixed for an hour. 5% of the monomer mix was added to the reactor when the temperature reached 85° C. At this point, a solution of 0.16 grams of ammonium persulfate in 37.90 grams water was added to the reactor. Reactor was then held under nitrogen at 85° C. for 15 mins. At the end of the 15 minutes, rest of the monomer mix was feed over 45 minutes. Concurrently, an initiator solution containing 0.08 grams of ammonium persulfate dissolved in 41.96 grams of water was added over 70 minutes. A nitrogen sparge is continued during these additions. The reaction mixture was then cooked at 85° C. for an hour. The solution was cooled down to 75° C. and 0.07 grams of ammonium persulfate in 24.37 grams of water was added. The final product was a viscous, creamy white emulsion with 20% solids. The solution was diluted to 5% and neutralized to pH 3 by slow addition of citric acid. There was no rheology buildup.

Example 31

40 grams of low molecular weight ethyl hydroxyethyl cellulose (EHEC) Bermocoll® E230 from AkzoNobel was dispersed in 837.5 grams of water containing 0.8 grams of sodium sulfate in a 1 liter reactor equipped with stirrer and a heating mantle. The mixture was heated to 85° C. while sparging with nitrogen. 0.1781 grams of ferrous ammonium sulfate hexahydrate dissolved in 10.57 grams of water and 4.15 grams of 35% hydrogen peroxide dissolved in 26.51 grams of water was added. This was then held under nitrogen at 85° C. for 15 minutes to depolymerize the ethyl hydroxyethyl cellulose. A monomer feed containing 48.61 grams of methacrylic acid, 60.17 grams of ethyl acrylate, 0.11 grams of diallyl phthalate and 10.72 grams of C18 alcohol with 20 EO itaconate (associative monomer) was then added over 45 minutes. Concurrently, an initiator solution containing 3.35 grams of 35% hydrogen peroxide dissolved in 21.42 grams of water was added over 60 minutes. A nitrogen sparge is continued during these additions. The reaction mixture was then cooked at 90° C. for an hour. The solution was cooled down to 75° C. The final product separated out in to an aqueous top phase and a bottom phase that is an opaque white paste which we term the aqueous emulsion paste. This aqueous emulsion paste phase had 25.04% polymer with the rest being water. The polymer portion of this aqueous paste was diluted to 2% and neutralized to pH 8 by slow addition of 10% NaOH. The result solution formed a gel which had a viscosity of 33,600 cps at 0.5 rpm as measured by a Brookfield viscometer. The polymer of the aqueous emulsion paste remained a paste for 3 months and longer and was easily redispersed in water on dilution.

Example 32

40 grams of low molecular weight ethyl hydroxyethyl cellulose (EHEC) Bermocoll® E230 from AkzoNobel was dispersed in 822.5 grams of water containing 4.0 grams of sodium sulfate in a 1 liter reactor equipped with stirrer and a heating mantle. The mixture was heated to 85° C. while sparging with nitrogen. 0.1781 grams of ferrous ammonium sulfate hexahydrate dissolved in 10.57 grams of water and 4.15 grams of 35% hydrogen peroxide dissolved in 26.51 grams of water was added. When the temperature reached 85° C., a monomer feed containing 48.61 grams of methacrylic acid, 60.17 grams of ethyl acrylate, 0.11 grams of diallyl phthalate and 10.72 grams of C18 alcohol with 20 EO itaconate (associative monomer) was then added over 45 minutes. Concurrently, an initiator solution containing 3.35 grams of 35% hydrogen peroxide dissolved in 21.42 grams of water was added over 60 minutes. A nitrogen sparge is continued during these additions. The reaction mixture was then cooked at 90° C. for an hour. The solution was cooled down to 75° C. and 0.31 grams of 70% tert butyl hydroperoxide in 10.00 grams of water was added. A solution of 0.14 grams of erythorbic acid dissolved in 10.00 grams of water was added over 1 hour and then the reaction was held at 70° C. for 30 minutes. The final product separated out in to an aqueous top phase and a bottom phase that is an opaque white paste which we term the aqueous emulsion paste. This aqueous emulsion paste phase had 18.1% polymer with the rest being water.

Example 33

40 grams of low molecular weight ethyl hydroxyethyl cellulose (EHEC) Bermocoll® E230 from AkzoNobel was dispersed in 837.5 grams of water containing 0.8 grams of sodium sulfate in a 1 liter reactor equipped with stirrer and a heating mantle. The mixture was heated to 85° C. while sparging with nitrogen. 0.1781 grams of ferrous ammonium sulfate hexahydrate dissolved in 10.57 grams of water and 4.15 grams of 35% hydrogen peroxide dissolved in 26.51 grams of water was added. This was then held under nitrogen at 85° C. for 30 minutes to depolymerize the ethyl hydroxyethyl cellulose. A monomer feed containing 48.61 grams of methacrylic acid, 60.17 grams of ethyl acrylate, 0.11 grams of diallyl phthalate and 10.72 grams of C18 alcohol with 20 EO itaconate (associative monomer) was then added over 45 minutes. Concurrently, an initiator solution containing 3.35 grams of 35% hydrogen peroxide dissolved in 21.42 grams of water was added over 60 minutes. A nitrogen sparge is continued during these additions. The reaction mixture was then cooked at 90° C. for an hour. The final product separated out in to an aqueous top phase and a bottom phase that is an opaque white paste which we term the aqueous emulsion paste. This aqueous emulsion paste phase had 26.5% polymer with the rest being water.

Example 34

40 grams of a low molecular weight ethyl hydroxyethyl cellulose (EHEC) Bermocoll® E230 from AkzoNobel was dispersed in 837.5 grams of water containing 20 grams of sodium sulfate in a 1 liter reactor equipped with stirrer and a heating mantle. The mixture was heated to 85° C. while sparging with nitrogen. 0.1781 grams of ferrous ammonium sulfate hexahydrate dissolved in 10.57 grams of water and 4.16 grams of 35% hydrogen peroxide dissolved in 26.51 grams of water was added. This was then held under nitrogen at 85° C. for 15 minutes to depolymerize the ethyl hydroxyethyl cellulose. A monomer feed containing 48.77 grams of methacrylic acid, 60.36 grams of ethyl acrylate, 0.12 grams of diallyl phthalate and 10.75 grams of C18 alcohol with 20 EO itaconate (associative monomer) was then added over 45 minutes. Concurrently, an initiator solution containing 3.36 grams of 35% hydrogen peroxide dissolved in 21.42 grams of water was added over 110 minutes. A nitrogen sparge is continued during these additions. The reaction mixture was then cooked at 90° C. for an hour. The final product separated out in to an aqueous top phase and a bottom phase that is an opaque white paste which we term the aqueous emulsion paste. This aqueous emulsion paste phase had 24.3% polymer with the rest being water.

Example 35

25.26 grams of low molecular weight ethyl hydroxyethyl cellulose (EHEC) Bermocoll® E230 from AkzoNobel was dispersed in 837.5 grams of water containing 0.48 grams of sodium sulfate in a 1 liter reactor equipped with stirrer and a heating mantle. The mixture was heated to 85° C. while sparging with nitrogen. 0.1069 grams of ferrous ammonium sulfate hexahydrate dissolved in 10.57 grams of water and 4.72 grams of 35% hydrogen peroxide dissolved in 26.51 grams of water was added. This was then held under nitrogen at 85° C. for 15 minutes to depolymerize the ethyl hydroxyethyl cellulose. A monomer feed containing 55.27 grams of methacrylic acid, 68.41 grams of ethyl acrylate, 0.13 grams of diallyl phthalate and 12.18 grams of C18 alcohol with 20 EO itaconate (associative monomer) was then added over 45 minutes. Concurrently, an initiator solution containing 3.81 grams of 35% hydrogen peroxide dissolved in 21.42 grams of water was added over 110 minutes. A nitrogen sparge is continued during these additions. The reaction mixture was then cooked at 90° C. for an hour. The final product separated out in to an aqueous top phase and a bottom phase that is an opaque white paste which we term the aqueous emulsion paste. This aqueous emulsion paste phase had 22.3% polymer with the rest being water.

Example 36

15.16 grams of low molecular weight ethyl hydroxyethyl cellulose (EHEC) Bermocoll® E230 from AkzoNobel was dispersed in 837.5 grams of water containing 0.29 grams of sodium sulfate in a 1 liter reactor equipped with stirrer and a heating mantle. The mixture was heated to 85° C. while sparging with nitrogen. 0.0641 grams of ferrous ammonium sulfate hexahydrate dissolved in 10.57 grams of water and 5.05 grams of 35% hydrogen peroxide dissolved in 26.51 grams of water was added. This was then held under nitrogen at 85° C. for 15 minutes to depolymerize the ethyl hydroxyethyl cellulose. A monomer feed containing 59.18 grams of methacrylic acid, 73.24 grams of ethyl acrylate, 0.14 grams of diallyl phthalate and 13.04 grams of C18 alcohol with 20 EO itaconate (associative monomer) was then added over 45 minutes. Concurrently, an initiator solution containing 3.81 grams of 35% hydrogen peroxide dissolved in 21.42 grams of water was added over 110 minutes. A nitrogen sparge is continued during these additions. The reaction mixture was then cooked at 90° C. for an hour. The final product separated out in to an aqueous top phase and a bottom phase that is an opaque white paste which we term the aqueous emulsion paste. This aqueous emulsion paste phase had 26.3% polymer with the rest being water.

Example 37

38.74 grams of low molecular weight ethyl hydroxyethyl cellulose (EHEC) Bermocoll® E230 from AkzoNobel was dispersed in 770.5 grams of water containing 0.74 grams of sodium sulfate in a 1 liter reactor equipped with stirrer and a heating mantle. The mixture was heated to 85° C. while sparging with nitrogen. 0.1639 grams of ferrous ammonium sulfate hexahydrate dissolved in 9.72 grams of water and 3.82 grams of 35% hydrogen peroxide dissolved in 24.39 grams of water was added. This was then held under nitrogen at 85° C. for 5 minutes to depolymerize the ethyl hydroxyethyl cellulose. A monomer feed containing 44.73 grams of methacrylic acid, 55.36 grams of ethyl acrylate, 0.11 grams of diallyl phthalate and 9.86 grams of $C_{18}$ alcohol with 20 EO itaconate (associative monomer) was then added over 45 minutes. Concurrently, an initiator solution containing 3.08 grams of 35% hydrogen peroxide dissolved in 19.70 grams of water was added over 60 minutes. A nitrogen sparge is continued during these additions. The reaction mixture was then cooked at 90° C. for an hour. The solution was cooled down to 75° C. and 0.38 grams of 70% tert butyl hydroperoxide in 1.90 grams of water was added. A solution of 0.17 grams of erythorbic acid dissolved in 12.62 grams of water was added over 1 hour and then the reaction was held at 70° C. for 30 minutes. The final product separated out in to an aqueous top phase and a bottom phase that is an opaque white paste which we term the aqueous emulsion paste. This aqueous emulsion paste phase had 27.5% polymer with the rest being water

Example 38

38.74 grams of low molecular weight ethyl hydroxyethyl cellulose (EHEC) Bermocoll® E230 from AkzoNobel was dispersed in 770.5 grams of water containing 0.74 grams of sodium sulfate in a 1 liter reactor equipped with stirrer and a heating mantle. The mixture was heated to 85° C. while sparging with nitrogen. 0.1639 grams of ferrous ammonium sulfate hexahydrate dissolved in 9.72 grams of water and 3.82 grams of 35% hydrogen peroxide dissolved in 24.39 grams of water was added. This was then held under nitrogen at 85° C. for 60 minutes to depolymerize the ethyl hydroxyethyl cellulose. A monomer feed containing 44.73 grams of methacrylic acid, 55.36 grams of ethyl acrylate, 0.11 grams of diallyl phthalate and 9.86 grams of $C_{18}$ alcohol with 20 EO itaconate (associative monomer) was then added over 45 minutes. Concurrently, an initiator solution containing 3.08 grams of 35% hydrogen peroxide dissolved in 19.70 grams of water was added over 60 minutes. A nitrogen sparge is continued during these additions. The reaction mixture was then cooked at 90° C. for an hour. The solution was cooled down to 75° C. and 0.38 grams of 70% tert butyl hydroperoxide in 1.90 grams of water was added. A solution of 0.17 grams of erythorbic acid dissolved in 12.62 grams of water was added over 1 hour and then the reaction was held at 70° C. for 30 minutes. The final product separated out in to an aqueous top phase and a bottom phase that is an opaque white paste which we term the aqueous emulsion paste. This aqueous emulsion paste phase had 28.7% polymer with the rest being water.

Example 39

The polymers of this invention were compared to the performance of a commercial polymer (Alcogum L-344 from AkzoNobel Surface Chemistry) in the paint formulation shown below in Table 9.

TABLE 9

| Materials | Weight percent |
|---|---|
| Water | 27.85 |
| Cellulose ether (Prime3500 from AkzoNobel) | 0.3 |
| 2-amino-2-methyl-1-propanol (AMP95) | 0.15 |
| Defoamer Dispelair CF-246 from Blackburn Chemicals Ltd. | 0.2 |
| Dispersant sodium polyacrylate | 0.5 |
| Wetting agent (EF-406 from Dow) | 0.2 |
| Titanium dioxide (Tiona 595 from Cristal Global) | 18 |
| Calcium carbonate (CC-1000) | 15 |
| Kaolin (Jufeng from Shanxi Jufeng Kaolin Co) | 6 |
| Defoamer (Dispelair CF-246) | 0.2 |
| Bactericide 1 2-benzisothiazol-3(2h)-one | 0.2 |
| Coalescing agent (Texanol from Eastman) | 2 |
| Propylene glycol (PG) | 1 |
| Acrylic Emulsion (Primal AC-261 from Dow) | 25 |
| Polymer (active) | 0.12 |
| Water | rest |

The paint was made based on the above exterior wall paint formulation. The pH of the final formulation was adjusted to range 8.5~8.8 as shown below in Table 10.

TABLE 10

| | Alcogum L-344 | Example 7 | Example 13 |
|---|---|---|---|
| pH | 8.58 | 8.62 | 8.77 |

1. ICI Viscosity

The ICI viscosity measured by an ICI viscometer in Pascals is evaluated under high shear rate. This corresponds to the processes of roller coating and spraying during the end use application.

TABLE 11

| Polymer | ICI viscosity (Pa) |
|---|---|
| Alcogum L-344 | 0.58 |
| Example 7 | 0.58 |
| Example 13 | 0.59 |

As shown in Table 11, the ICI viscosity of paints with Alcogum and the two polymers of this invention are nearly identical.

2. Brookfield Viscosity

Brookfield viscosity (measured in centipoise/cP) is evaluated under low shear rate and is a measure of levelling, sagging and settling in paint and coating applications. The meter is Brookfield viscometer using cP as a unit. Table 12 shows the Brookfield viscosity of paints under different rotate speed conditions (0.3 rpm, 6 rpm and 60 rpm).

TABLE 12

| | Brookfield Viscosity (cP) | | | Ratio |
|---|---|---|---|---|
| Polymer | 0.3 rpm | 6 rpm | 60 rpm | (0.3/60 rpm) |
| L-344 | 112000 | 12100 | 2480 | 45.16 |
| Example 7 | 115000 | 12933 | 2707 | 42.48 |
| Example 13 | 130000 | 13600 | 2760 | 47.10 |

The Ratio listed in the last column of Table 12 is the ratio of the 0.3 rpm viscosity reading over the 60 rpm reading. The closer that value the more similar the rheology response on the formulation. The Brookfield viscosity response of the two polymers of this invention is around that of the commercial polymer.

3. Pigments Floating Problems

Pigments were added to these paint formulations. The formulations were then observed to detect pigment flotation issues. No pigment floating issues was found.

4. Water Separation

TABLE 13

| | Water separation (mm) | |
|---|---|---|
| Polymer | Room temperature | 50° C. (60 days) |
| Alcogum L-344 | 0 | 4 |
| Example 7 | 0 | 1 |
| Example 13 | 0 | 2 |

As shown in Table 13, all the polymers have no water separation problems at room temperature. However, after 60 days at 50° C. the paints having Polymers of this invention have less water separation compared to the paint containing Alcogum L-344. This degree of water separation in this test should have no impact on the paint performance as it can be blended well before application.

In summary, the performance of the polymers of this invention is similar to that of a commercial polymer in paint formulations.

Example 40

80 grams of a low molecular weight ethyl hydroxyethyl cellulose (EHEC) Bermocoll® E230 from AkzoNobel (weight average molecular weight of approximately 300,000) was dispersed in 1675 grams of water containing 1.6 grams of sodium sulfate in a 2 liter reactor equipped with stirrer and a heating mantle. The mixture was heated to 85 C while sparging with nitrogen. 0.338 grams of ferrous ammonium sulfate hexahydrate dissolved in 21 grams of water and 8.3 grams of 35% hydrogen peroxide dissolved in 53 grams of water was added. This was then held under nitrogen at 85° C. for 15 minutes to depolymerize the ethyl hydroxyethyl cellulose. A monomer feed containing 97.2 grams of methacrylic acid, 120 grams of n-butyl acrylate, 0.2 grams of diallyl phthalate and 21.43 grams of $C_{18}$ alcohol with 20EO itaconate (associative monomer) was then added over 45 minutes. Concurrently, an initiator solution containing 6.7 grams of 35% hydrogen peroxide dissolved in 42.8 grams of water was added over 110 minutes. A nitrogen sparge is continued during these additions. The reaction mixture was then cooked at 90° C. for an hour. The reaction product was allowed to cool overnight and separates out in to an aqueous top phase and a bottom phase that is an opaque white paste which we term the aqueous emulsion paste composition. This aqueous emulsion paste composition had 21.2% polymer with the rest being water. A sample of this aqueous emulsion paste was diluted to 2% polymer in water and then neutralized with 50% NaOH to pH 8. The Brookfield viscosity of this solution was 3970 cP at 10 rpm.

Example 41

80 grams of a low molecular weight ethyl hydroxyethyl cellulose (EHEC) Bermocoll® E230 from AkzoNobel (weight average molecular weight of approximately 300,000) was dispersed in 1675 grams of water containing 1.6 grams of sodium sulfate in a 2 liter reactor equipped with stirrer and a heating mantle. The mixture was heated to 85° C. while sparging with nitrogen. 0.356 grams of ferrous ammonium sulfate hexahydrate dissolved in 21 grams of water and 8.3 grams of 35% hydrogen peroxide dissolved in 53 grams of water was added. This was then held under nitrogen at 85° C. for 15 minutes to depolymerize the ethyl hydroxyethyl cellulose. A monomer feed containing 97.2 grams of methacrylic acid, 154 grams of n-butyl acrylate, 0.2 grams of diallyl phthalate and 21.43 grams of $C_{18}$ alcohol with 20EO itaconate (associative monomer) was then added over 45 minutes. Concurrently, an initiator solution containing 6.7 grams of 35% hydrogen peroxide dissolved in 42.8 grams of water was added over 110 minutes. A nitrogen sparge is continued during these additions. The reaction mixture was then cooked at 90° C. for an hour. The reaction product was allowed to cool overnight and separates out in to an aqueous top phase and a bottom phase that is an opaque white paste which we term the aqueous emulsion paste composition. This aqueous emulsion paste composition had 23.9% polymer with the rest being water. A sample of this aqueous emulsion paste was diluted to 2% polymer in water and then neutralized with 50% NaOH to pH 8. The Brookfield viscosity of this solution was 4360 cP at 10 rpm.

Example 42

108 grams of a 85% Perfectamyl A4692 (oxidized potato starch from Avebe with a weight average molecular weight of 510,000) was dissolved in 1300 grams of water in a 2 liter reactor equipped with stirrer and a heating mantle. The mixture was heated to 85° C. while sparging with nitrogen for one hour. A monomer solution containing 101.7 grams of methacrylic acid, 125.9 grams of n-butyl acrylate, 0.24 grams of diallyl phthalate and 22.4 grams of $C_{18}$ alcohol with 20EO itaconate (associative monomer) was prepared. 5 weight percent of this monomer mixture was added to the reactor. At the same time 0.27 grams of ammonium persulfate dissolved in 19.8 grams of water was added. The reaction mixture was held at 85° C. for 15 minutes under nitrogen. The rest of the monomer was then added over 90 minutes. Concurrently, an initiator solution containing 0.17 grams of ammonium persulfate dissolved in 45 grams of water was added over 120 minutes. A nitrogen sparge was continued during these additions. The reaction mixture was then cooked at 85° C. for an hour. A solution of 0.17 grams of ammonium persulfate dissolved in 8 grams of water was added over 1 hour and then the reaction was held at 85° C. for 30 minutes. The final product was a stable emulsion composition with 19% solids. A sample of this emulsion was diluted to 2% polymer in water and then neutralized with 50% NaOH to pH 8. The Brookfield viscosity of this solution was 2932 cP at 10 rpm.

Example 43

108 grams of a 85% Perfectamyl A4692 (oxidized potato starch from Avebe with a weight average molecular weight of 510,000) was dissolved in 1400 grams of water in a 2 liter reactor equipped with stirrer and a heating mantle. The mixture was heated to 85° C. while sparging with nitrogen for one hour. A monomer solution containing 101.7 grams of methacrylic acid, 161 grams of n-butyl acrylate, 0.24 grams of diallyl phthalate and 22.4 grams of $C_{18}$ alcohol with 20EO itaconate (associative monomer) was prepared. 5 weight percent of this monomer mixture was added to the reactor. At the same time 0.27 grams of ammonium persulfate dissolved in 19.8 grams of water was added. The reaction mixture was held at 85° C. for 15 minutes under nitrogen. The rest of the monomer was then added over 90 minutes. Concurrently, an initiator solution containing 0.17 grams of ammonium persulfate dissolved in 45 grams of water was added over 120 minutes. A nitrogen sparge was continued during these additions. The reaction mixture was then cooked at 85° C. for an hour. A solution of 0.17 grams of ammonium persulfate dissolved in 8 grams of water was added over 1 hour and then the reaction was held at 85° C. for 30 minutes. The final product was a stable emulsion composition with 19.2% solids. A sample of this emulsion was diluted to 2% polymer in water and then neutralized with 50% NaOH to pH 8. The Brookfield viscosity of this solution was 2760 cP at 10 rpm.

Example 44

33.6 grams of a low molecular weight ethyl hydroxyethyl cellulose (EHEC) Bermocoll® E230 from AkzoNobel (weight average molecular weight of approximately 300,000) was dispersed in 703.5 grams of water containing 0.67 grams of sodium sulfate in a 1 liter reactor equipped with stirrer and a heating mantle. The mixture was heated to 85° C. while sparging with nitrogen. 0.15 grams of ferrous ammonium sulfate hexahydrate dissolved in 9 grams of water and 3.5 grams of 35% hydrogen peroxide dissolved in 22 grams of water was added. This was then held under nitrogen at 85° C. for 15 minutes to depolymerize the ethyl hydroxyethyl cellulose. A monomer feed containing 66.6 grams of methacrylic acid, 24.8 grams of ethyl acrylate, 0.1 grams of diallyl phthalate and 9 grams of $C_{18}$ alcohol with 20EO itaconate (associative monomer) was then added over 45 minutes. The ethyl acrylate was 20 weight percent of the total monomer. Concurrently, an initiator solution containing 2.8 grams of 35% hydrogen peroxide dissolved in 18 grams of water was added over 110 minutes. A nitrogen sparge is continued during these additions. The reaction mixture was then cooked at 90° C. for an hour. The reaction product was allowed to cool overnight and separates out in to an aqueous top phase of 232 grams and a bottom aqueous emulsion paste composition of 580 grams. This aqueous emulsion paste composition had 20% polymer with the rest being water. A sample of this aqueous emulsion paste was diluted to 2% polymer in water and then neutralized with 50% NaOH to pH 8. The Brookfield viscosity of this solution was 1720 cP at 10 rpm.

Example 45

33.6 grams of a low molecular weight starch (maltodextrin) Star Dri 5 (from Tate and Lyle) was dissolved in 703.5 grams of water containing 0.67 grams of sodium sulfate in a 1 liter reactor equipped with stirrer and a heating mantle.

The mixture was heated to 85° C. while sparging with nitrogen. 0.15 grams of ferrous ammonium sulfate hexahydrate dissolved in 9 grams of water and 3.5 grams of 35% hydrogen peroxide dissolved in 22 grams of water was added. This was then held under nitrogen at 85° C. for 15 minutes. A monomer feed containing 73.8 grams of methacrylic acid, 18.4 grams of ethyl acrylate, 0.1 grams of diallyl phthalate and 9 grams of $C_{18}$ alcohol with 20EO itaconate (associative monomer) was then added over 45 minutes. The ethyl acrylate was 20 weight percent of the total monomer. Concurrently, an initiator solution containing 2.8 grams of 35% hydrogen peroxide dissolved in 18 grams of water was added over 110 minutes. A nitrogen sparge is continued during these additions. The reaction mixture was then cooked at 85° C. for an hour. The reaction product was an emulsion with 14.3% solids. A sample of this emulsion was diluted to 2% polymer in water and then neutralized with 50% NaOH to pH 8. The Brookfield viscosity of this solution was 1832 cP at 10 rpm.

Example 46

33.6 grams of a low molecular weight starch (maltodextrin) Star Dri 5 (from Tate and Lyle) was dissolved in 703.5 grams of water containing 0.67 grams of sodium sulfate in a 1 liter reactor equipped with stirrer and a heating mantle. The mixture was heated to 85° C. while sparging with nitrogen. 0.15 grams of ferrous ammonium sulfate hexahydrate dissolved in 9 grams of water and 3.5 grams of 35% hydrogen peroxide dissolved in 22 grams of water was added. This was then held under nitrogen at 85° C. for 15 minutes. A monomer feed containing 79.9 grams of methacrylic acid, 12.3 grams of ethyl acrylate, 0.1 grams of diallyl phthalate and 9 grams of $C_{18}$ alcohol with 20EO itaconate (associative monomer) was then added over 45 minutes. The ethyl acrylate was 12 weight percent of the total monomer. Concurrently, an initiator solution containing 2.8 grams of 35% hydrogen peroxide dissolved in 18 grams of water was added over 110 minutes. A nitrogen sparge is continued during these additions. The reaction mixture was then cooked at 85° C. for an hour. The reaction product was an emulsion with 14.3% solids. A sample of this emulsion was diluted to 2% polymer in water and then neutralized with 50% NaOH to pH 8. The Brookfield viscosity of this solution was 206 cP at 10 rpm. This example shows that a polymer containing just ethylacrylate and methacrylic acid without an associative monomer requires greater than 12 weight percent ethylacrylate based on the weight of the total monomer to give a viscosity of 500 cps at 10 rpm. This lower level of ethyl acrylate or hydrophobic monomer will change if an associative monomer is added or the weight percent of the polysaccharide or the type of polysaccharide is changed.

Example 47

65.6 grams of 85% Perfectamyl A4692 (oxidized potato starch from Avebe with a weight average molecular weight of 510,000) was dissolved in 692 grams of water in a 1 liter reactor equipped with stirrer and a heating mantle. The mixture was heated to 85° C. while sparging with nitrogen for one hour. A monomer solution containing 48.3 grams of methacrylic acid, 109.5 grams of ethyl acrylate and 0.62 grams of trimethylol propane triacrylate and was added over 90 minutes. Concurrently, an initiator solution containing 0.66 grams of ammonium persulfate dissolved in 65 grams of water was added over 120 minutes. A nitrogen sparge was continued during these additions. The reaction mixture was then cooked at 85° C. for 2 hours.

Example 48

54 grams of 85% Perfectamyl 4692 (oxidized potato starch from Avebe) was dissolved in 668 grams of water in a 1 liter reactor equipped with stirrer and a heating mantle. The mixture was heated to 85° C. while sparging with nitrogen for one hour. A monomer solution containing 45.2 grams of methacrylic acid, 21.1 grams of methyl acrylate, 0.12 grams of diallyl phthalate, 49.2 grams of n-butyl acrylate and 22.4 grams of a associative monomer mixture which is 50% $C_{16-18}$ alcohol with 20EO, 25% methacrylic acid and 25% water was prepared. 5 weight percent of this monomer mixture was added to the reactor. At the same time 0.41 grams of ammonium persulfate dissolved in 10 grams of water was added. The reaction mixture was held at 85° C. for 15 minutes under $N_2$. The rest of the monomer was then added over 90 minutes. Concurrently, an initiator solution containing 0.26 grams of ammonium persulfate dissolved in 23 grams of water was added over 120 minutes. A nitrogen sparge was continued during these additions. The reaction mixture was then cooked at 85° C. for an hour. A solution of 0.24 grams of ammonium persulfate dissolved in 4 grams of water was added over 15 minutes and then the reaction was held at 85° C. for 30 minutes. The final product was an emulsion composition with 19.4% solids and was a stable emulsion for over 6 months.

Example 49

52.8 grams of 85% Perfectamyl 4692 (oxidized potato starch from Avebe) was dissolved in 671 grams of water in a 1 liter reactor equipped with stirrer and a heating mantle. The mixture was heated to 85° C. while sparging with nitrogen for one hour. A monomer solution containing 55.6 grams of methacrylic acid, 0.12 grams of diallyl phthalate, 62.0 grams of n-butyl acrylate and 21.8 grams of an associative monomer mixture which is 50% $C_{16-18}$ alcohol with 20EO, 25% methacrylic acid and 25% water was prepared. 5 weight percent of this monomer mixture was added to the reactor. At the same time 0.37 grams of ammonium persulfate dissolved in 10 grams of water was added. The reaction mixture was held at 85° C. for 15 minutes under $N_2$. The rest of the monomer was then added over 90 minutes. Concurrently, an initiator solution containing 0.25 grams of ammonium persulfate dissolved in 23 grams of water was added over 120 minutes. A nitrogen sparge was continued during these additions. The reaction mixture was then cooked at 85° C. for an hour. A solution of 0.24 grams of ammonium persulfate dissolved in 4 grams of water was added over 15 minutes and then the reaction was held at 85° C. for 30 minutes. The final product was an emulsion composition with 19.4% solids and was a stable emulsion for over 6 months.

Example 50

52.9 grams of 85% Perfectamyl 4692 (oxidized potato starch from Avebe) was dissolved in 631 grams of water in a 1 liter reactor equipped with stirrer and a heating mantle. The mixture was heated to 85° C. while sparging with nitrogen for one hour. A monomer solution containing 55.6 grams of methacrylic acid, 20.7 grams of methyl acrylate, 0.12 grams of diallyl phthalate, 31.2 grams of n-butyl acrylate and 21.8 grams of an associative monomer mixture which is 50% $C_{16-18}$ alcohol with 20EO, 25% methacrylic acid and 25% water was prepared. 5 weight percent of this monomer mixture was added to the reactor. At the same time 0.40 grams of ammonium persulfate dissolved in 10 grams of water was added. The reaction mixture was held at 85° C. for 15 minutes under $N_2$. The rest of the monomer was then added over 90 minutes. Concurrently, an initiator solution containing 0.25 grams of ammonium persulfate dissolved in 23 grams of water was added over 120 minutes. A nitrogen sparge was continued during these additions. The reaction mixture was then cooked at 85° C. for an hour. A solution of 0.24 grams of ammonium persulfate dissolved in 4 grams of water was added over 15 minutes and then the reaction was held at 85° C. for 30 minutes. The final product was an emulsion composition with 19.2% solids and was a stable emulsion for over 6 months.

Example 51

56.9 grams of 85% Perfectamyl 4692 (oxidized potato starch from Avebe) was dissolved in 684 grams of water in a 1 liter reactor equipped with stirrer and a heating mantle. The mixture was heated to 85° C. while sparging with nitrogen for one hour. A monomer solution containing 53.5 grams of methacrylic acid, 66.3 grams of ethyl acrylate and 0.126 grams of diallyl phthalate was prepared. 5 weight percent of this monomer mixture was added to the reactor. At the same time 0.14 grams of ammonium persulfate dissolved in 10 grams of water was added. The reaction mixture was held at 85° C. for 15 minutes under $N_2$. The rest of the monomer was then added over 90 minutes. Concurrently, an initiator solution containing 0.084 grams of ammonium persulfate dissolved in 24 grams of water was added over 120 minutes. A nitrogen sparge was continued during these additions. The reaction mixture was then cooked at 85° C. for an hour. A solution of 0.084 grams of ammonium persulfate dissolved in 4 grams of water was added over 15 minutes and then the reaction was held at 85° C. for 30 minutes. The final product was an emulsion composition with 18.1% solids and was a stable emulsion for over 6 months.

Example 52

65.4 grams of 85% Perfectamyl 4692 (oxidized potato starch from Avebe) was dissolved in 665 grams of water in a 1 liter reactor equipped with stirrer and a heating mantle. The mixture was heated to 85° C. while sparging with nitrogen for one hour. A monomer solution containing 61.5 grams of methacrylic acid, 65.5 grams of methyl acrylate and 0.145 grams of diallyl phthalate was prepared. 5 weight percent of this monomer mixture was added to the reactor. At the same time 0.16 grams of ammonium persulfate dissolved in 12 grams of water was added. The reaction mixture was held at 85° C. for 15 minutes under $N_2$. The rest of the monomer was then added over 90 minutes. Concurrently, an initiator solution containing 0.1 grams of ammonium persulfate dissolved in 27.7 grams of water was added over 120 minutes. A nitrogen sparge was continued during these additions. The reaction mixture was then cooked at 85° C. for an hour. A solution of 0.1 grams of ammonium persulfate dissolved in 4 grams of water was added over 15 minutes and then the reaction was held at 85° C. for 30 minutes. The final product was an emulsion composition with 19.9% solids and was a stable emulsion for over 6 months.

Example 52

56.2 grams of 85% Perfectamyl 4692 (oxidized potato starch from Avebe) was dissolved in 676 grams of water in a 1 liter reactor equipped with stirrer and a heating mantle. The mixture was heated to 85° C. while sparging with nitrogen for one hour. A monomer solution containing 52.9 grams of methacrylic acid, 56.3 grams of methyl acrylate, 11.7 grams of $C_{18}$ alcohol with 20EO itaconate (associative monomer), and 0.125 grams of diallyl phthalate was prepared. 5 weight percent of this monomer mixture was added to the reactor. At the same time 0.14 grams of ammonium persulfate dissolved in 10 grams of water was added. The reaction mixture was held at 85° C. for 15 minutes under $N_2$. The rest of the monomer was then added over 90 minutes. Concurrently, an initiator solution containing 0.89 grams of ammonium persulfate dissolved in 24 grams of water was added over 120 minutes. A nitrogen sparge was continued during these additions. The reaction mixture was then cooked at 85° C. for an hour. A solution of 0.08 grams of ammonium persulfate dissolved in 4 grams of water was added over 15 minutes and then the reaction was held at 85° C. for 30 minutes. The final product was an emulsion composition with 18.2% solids and was a stable emulsion for over 6 months.

Example 53

55.7 grams of 85% Perfectamyl 4692 (oxidized potato starch from Avebe) was dissolved in 680 grams of water in a 1 liter reactor equipped with stirrer and a heating mantle. The mixture was heated to 85° C. while sparging with nitrogen for one hour. A monomer solution containing 53.5 grams of methacrylic acid, 66.3 grams of ethyl acrylate and 0.126 grams of diallyl phthalate was prepared. An initiator solution containing 0.58 grams of ammonium persulfate dissolved in 52 grams of water was prepared. 5 weight percent of the monomer mixture above was added to the reactor and held for 15 minutes. 9 weight percent of the initiator mixture above was added to the reactor and held for 15 minutes. The rest of the monomer was then added over 90 minutes. Concurrently the rest of the initiator solution was added over 90 minutes. A nitrogen sparge was continued during these additions. The reaction mixture was then cooked at 85° C. for an hour and then 2 hours at 70° C. The final product was an emulsion composition with 19.8% solids and was a stable emulsion for over 6 months.

Example 54

55.7 grams of 85% Perfectamyl 4692 (oxidized potato starch from Avebe) was dissolved in 680 grams of water in a 1 liter reactor equipped with stirrer and a heating mantle. The mixture was heated to 85° C. while sparging with nitrogen for one hour. A monomer solution containing 50.7 grams of methacrylic acid, 87.6 grams of ethyl acrylate and 0.55 grams of trimethylol propyl triacrylate (TMPTA) was prepared. An initiator solution containing 0.58 grams of ammonium persulfate dissolved in 52 grams of water was prepared. The monomer solution was then added over 90 minutes. Concurrently the initiator solution was added over 90 minutes. A nitrogen sparge was continued during these additions. The reaction mixture was then cooked at 85° C. for an hour and then 2 hours at 70° C. The final product was an emulsion composition with 19.8% solids and was a stable emulsion for over 6 months.

Example 55

Evaluation of Samples in Examples 47 to 54 in Shampoo Formulation 200 grams of typical shampoo base was prepared by adding 59.58 grams of Deionized water to a 250 ml beaker. A small 1½ inch jiffy mixer blade was inserted into the beaker and attached to an overhead mixer. The batch was allowed to mix with a vortex extending to the middle of the beaker. Then 24.30 grams (3% active polymer) of Examples 1 to 8 was added and allowed to mix until uniform. This was followed by adding 62.74 grams of Sodium Laureth Sulfate (25.2% active Standapol ES-2 from Cognis Corporation, FairField, N.J.). This was allowed to mix until it was homogenous. Then 27.58 grams of Sodium Lauryl sulfate (Witconate WAC LA, Akzo Nobel, Houston, Tex.) was added and mixed until homogenous. Then 22.80 grams of Cocamidoproply Betaine (Crodateric CAB 30, Croda Inc, Edison, N.J.) was added an allowed to mix until homogenous. Then 1.0 grams of DMDM Hydantoin and IodopropynylButylcarbamate Glydant Plus (Liquid), Lonza Corp Allendale, N.J.) was added and the batch was mixed until homogenous. The pH was then adjusted to 6.5+/−0.25 using 25% sodium hydroxide (Fisher Scientific, Fairlawn, N.J.) as needed. Once the batch was uniform 2 grams of cosmetic beads, Floraspheres JoJoba MDS beads (Floratech, Chandler, Ariz.) were gently folded into the batch until they were evenly distributed throughout the batch.

To test the suspension properties of the cosmetic beads, the shampoo formulations were placed in a 45° C. oven and the dispersion of the beads was visually monitored for migration of the beads. The results are shown in Table 14. Any sample that showed migration of the beads was deemed a failure.

TABLE 14

| Polymer of Example | 45° C. Suspension Results |
|---|---|
| None | Did not suspend |
| Example 47 | Suspended for 90+ days |
| Example 48 | Suspended for 120+ days |
| Example 49 | Suspended for 90+ days |
| Example 50 | Suspended for 120+ days |
| Example 51 | Suspended for 120+ days |
| Example 52 | Suspended for 120+ days |
| Example 53 | Suspended for 120+ days |
| Example 54 | Suspended for 120+ days |

Example 56

55.7 grams of 85% Perfectamyl 4692 (oxidized potato starch from Avebe) was dissolved in 680 grams of water in a 1 liter reactor equipped with stirrer and a heating mantle. The mixture was heated to 85° C. while sparging with nitrogen for one hour. A monomer solution containing 50.7 grams of methacrylic acid, 87.6 grams of ethyl acrylate and 1.06 grams of polyethylene glycol diacrylate was prepared. An initiator solution containing 0.58 grams of ammonium persulfate dissolved in 52 grams of water was prepared. The monomer solution was then added over 90 minutes. Concurrently the initiator solution was added over 90 minutes. A nitrogen sparge was continued during these additions. The reaction mixture was then cooked at 85° C. for an hour and then 2 hours at 70° C. The final product was an emulsion composition with 19.5% solids and was a stable emulsion for over 6 months.

Example 57

66.9 grams of 85% Perfectamyl 4692 (oxidized potato starch from Avebe) was dissolved in 680 grams of water in a 1 liter reactor equipped with stirrer and a heating mantle. The mixture was heated to 85° C. while sparging with nitrogen for one hour. A monomer solution containing 47.3 grams of methacrylic acid, 81.2 grams of ethyl acrylate and 0.51 grams of trimethylol propyl triacrylate (TMPTA) was prepared. An initiator solution containing 0.58 grams of ammonium persulfate dissolved in 52 grams of water was prepared. The monomer solution was then added over 90 minutes. Concurrently the initiator solution was added over 90 minutes. A nitrogen sparge was continued during these additions. The reaction mixture was then cooked at 85° C. for an hour and then 2 hours at 70° C. The final product was an emulsion composition with 19.7% solids and was a stable emulsion for over 6 months.

Example 58

89.2 grams of 85% Perfectamyl 4692 (oxidized potato starch from Avebe) was dissolved in 675 grams of water in a 1 liter reactor equipped with stirrer and a heating mantle. The mixture was heated to 85° C. while sparging with nitrogen for one hour. A monomer solution containing 40.6 grams of methacrylic acid, 70.1 grams of ethyl acrylate and 0.44 grams of trimethylol propyl triacrylate (TMPTA) was prepared. An initiator solution containing 0.58 grams of ammonium persulfate dissolved in 52 grams of water was prepared. The monomer solution was then added over 90 minutes. Concurrently the initiator solution was added over 90 minutes. A nitrogen sparge was continued during these additions. The reaction mixture was then cooked at 85° C. for an hour and then 2 hours at 70° C. The final product was an emulsion composition with 19.6% solids and was a stable emulsion for over 6 months.

Example 59

111.5 grams of 83% Perfectamyl 4692 (oxidized potato starch from Avebe) was dissolved in 671.5 grams of water in a 1 liter reactor equipped with stirrer and a heating mantle. The mixture was heated to 85° C. while sparging with nitrogen for one hour. A monomer solution containing 33.8 grams of methacrylic acid, 58.4 grams of ethyl acrylate and 0.37 grams of trimethylol propyl triacrylate (TMPTA) was prepared. An initiator solution containing 0.58 grams of ammonium persulfate dissolved in 52.1 grams of water was prepared. The monomer solution was then added over 90 minutes. Concurrently the initiator solution was added over 90 minutes. A nitrogen sparge was continued during these additions. The reaction mixture was then cooked at 85° C. for 2 hours. The final product was an emulsion composition with 19.9% solids.

Example 60

57.2 grams of 80.9% PR1004B (oxidized potato starch from Avebe that is a higher molecular weight than Perfectamyl 4692) was dissolved in 675 grams of water in a 1 liter reactor equipped with stirrer and a heating mantle. The mixture was heated to 85° C. while sparging with nitrogen for one hour. A monomer solution containing 50.7 grams of methacrylic acid, 87.6 grams of ethyl acrylate and 0.55 grams of trimethylol propyl triacrylate (TMPTA) was prepared. An initiator solution containing 0.58 grams of ammonium persulfate dissolved in 52 grams of water was prepared. The monomer solution was then added over 90 minutes. Concurrently the initiator solution was added over 90 minutes. A nitrogen sparge was continued during these additions. The reaction mixture was then cooked at 85° C. for an hour and then 2 hours at 70° C. The final product was an emulsion composition with 19.4% solids.

Example 61

The polymer from examples 56 to 60 were evaluated in a shampoo formulation as described in Example 55. The results of this evaluation are detailed in Table 15 below.

TABLE 15

| Polymer of Example | 45° C. Suspension Results |
|---|---|
| None | Did not suspend |
| Example 56 | Suspended for 10+ days |
| Example 57 | Suspended for 10+ days |
| Example 58 | Suspended for 10+ days |
| Example 59 | Suspended for 10+ days |
| Example 60 | Suspended for 10+ days |

Example 62

89.2 grams of 83% Perfectamyl 4692 (oxidized potato starch from Avebe) was dissolved in 675.3 grams of water in a 1 liter reactor equipped with stirrer and a heating mantle. The mixture was heated to 85° C. while sparging with nitrogen for one hour. A monomer solution containing 40.6 grams of methacrylic acid, 70.1 grams of ethyl acrylate and 0.44 grams of trimethylol propyl triacrylate (TMPTA) was prepared. An initiator solution containing 0.58 grams of ammonium persulfate dissolved in 52.1 grams of water was prepared. The monomer solution was then added over 90 minutes. Concurrently the initiator solution was added over 90 minutes. A nitrogen sparge was continued during these additions. The reaction mixture was then cooked at 85° C. for an hour and then 2 hours at 70° C. The final product was an emulsion composition with 19.9% solids.

Example 63

111.5 grams of 83% Perfectamyl 4692 (oxidized potato starch from Avebe) was dissolved in 671.5 grams of water in a 1 liter reactor equipped with stirrer and a heating mantle. The mixture was heated to 85° C. while sparging with nitrogen for one hour. A monomer solution containing 33.8 grams of methacrylic acid, 58.4 grams of ethyl acrylate and 0.37 grams of trimethylol propyl triacrylate (TMPTA) was prepared. An initiator solution containing 0.58 grams of ammonium persulfate dissolved in 52.1 grams of water was prepared. The monomer solution was then added over 90 minutes. Concurrently the initiator solution was added over 90 minutes. A nitrogen sparge was continued during these additions. The reaction mixture was then cooked at 85° C. for two hours. The final product was an emulsion composition with 19.9% solids.

Example 64

62.4 grams of 80.9% PR1004B (a higher molecular weight oxidized potato starch from Avebe) was dissolved in 742.3 grams of water in a 1 liter reactor equipped with stirrer and a heating mantle. The mixture was heated to 85° C. while sparging with nitrogen for one hour. A monomer solution containing 55.3 grams of methacrylic acid, 95.5 grams of ethyl acrylate and 0.60 grams of trimethylol propyl triacrylate (TMPTA) was prepared. An initiator solution containing 0.64 grams of ammonium persulfate dissolved in 56.8 grams of water was prepared. The monomer solution was then added over 90 minutes. Concurrently the initiator solution was added over 90 minutes. A nitrogen sparge was continued during these additions. The reaction mixture was then cooked at 85° C. for two hours. The final product was an emulsion composition with 19.5% solids.

Example 65

74.9 grams of 80.9% PR1004B (a higher molecular weight oxidized potato starch from Avebe) was dissolved in 742.3 grams of water in a 1 liter reactor equipped with stirrer and a heating mantle. The mixture was heated to 85° C. while sparging with nitrogen for one hour. A monomer solution containing 51.6 grams of methacrylic acid, 89.1 grams of ethyl acrylate and 0.51 grams of trimethylol propyl triacrylate (TMPTA) was prepared. An initiator solution containing 0.64 grams of ammonium persulfate dissolved in 56.8 grams of water was prepared. The monomer solution was then added over 90 minutes. Concurrently the initiator solution was added over 90 minutes. A nitrogen sparge was continued during these additions. The reaction mixture was then cooked at 85° C. for two hours. The final product was an emulsion composition with 19.4% solids.

Example 66

55.8 grams of 83% Perfectamyl 4692 (oxidized potato starch from Avebe) was dissolved in 681 grams of water in a 1 liter reactor equipped with stirrer and a heating mantle. The mixture was heated to 85° C. while sparging with nitrogen for one hour. A monomer solution containing 50.7 grams of methacrylic acid, 87.6 grams of ethyl acrylate and 1.06 grams of polyethylene glycol 400 diacrylate was prepared. An initiator solution containing 0.58 grams of ammonium persulfate dissolved in 52.1 grams of water was prepared. The monomer solution was then added over 90 minutes. Concurrently the initiator solution was added over 90 minutes. A nitrogen sparge was continued during these additions. The reaction mixture was then cooked at 85° C. for an hour and then 2 hours at 70° C. The final product was an emulsion composition with 19.9% solids.

Example 67

60.8 grams of 83% Perfectamyl 4692 (oxidized potato starch from Avebe) was dissolved in 742.3 grams of water in a 1 liter reactor equipped with stirrer and a heating mantle. The mixture was heated to 85° C. while sparging with nitrogen for one hour. A monomer solution containing 55.3 grams of methacrylic acid, 95.6 grams of ethyl acrylate and 0.54 grams of pentaerythritol tetraacrylate was prepared. An initiator solution containing 0.64 grams of ammonium persulfate dissolved in 56.8 grams of water was prepared. The monomer solution was then added over 90 minutes. Concurrently the initiator solution was added over 90 minutes. A nitrogen sparge was continued during these additions. The reaction mixture was then cooked at 85° C. for two hours. The final product was an emulsion composition with 19.3% solids.

Example 68

60.8 grams of 83% Perfectamyl 4692 (oxidized potato starch from Avebe) was dissolved in 742.3 grams of water in a 1 liter reactor equipped with stirrer and a heating mantle. The mixture was heated to 85° C. while sparging with nitrogen for one hour. A monomer solution containing 55.3 grams of methacrylic acid, 95.6 grams of ethyl acrylate and 0.43 grams of dipentaerythritol pentaacrylate was prepared. An initiator solution containing 0.64 grams of ammonium persulfate dissolved in 56.8 grams of water was prepared. The monomer solution was then added over 90 minutes. Concurrently the initiator solution was added over 90 minutes. A nitrogen sparge was continued during these additions. The reaction mixture was then cooked at 85° C. for two hours. The final product was an emulsion composition with 19.8% solids.

Example 69

73.3 grams of 80.9% PR1004B (a higher molecular weight oxidized potato starch from Avebe) was dissolved in 800 grams of water in a 1 liter reactor equipped with stirrer and a heating mantle. The mixture was heated to 85° C. while sparging with nitrogen for one hour. A monomer solution containing 32.5 grams of methacrylic acid, 56.1 grams of ethyl acrylate and 0.35 grams of trimethylol propyl triacrylate (TMPTA) was prepared. An initiator solution containing 0.47 grams of ammonium persulfate dissolved in 41.7 grams of water was prepared. The monomer solution was then added over 90 minutes. Concurrently the initiator solution was added over 90 minutes. A nitrogen sparge was continued during these additions. The reaction mixture was then cooked at 85° C. for two hours. The final product was an emulsion composition with 14.3% solids.

Example 70

91.6 grams of 80.9% PR1004B (a higher molecular weight oxidized potato starch from Avebe) was dissolved in 800 grams of water in a 1 liter reactor equipped with stirrer and a heating mantle. The mixture was heated to 85° C. while sparging with nitrogen for one hour. A monomer solution containing 27.0 grams of methacrylic acid, 46.7 grams of ethyl acrylate and 0.29 grams of trimethylol propyl triacrylate (TMPTA) was prepared. An initiator solution containing 0.47 grams of ammonium persulfate dissolved in 41.7 grams of water was prepared. The monomer solution was then added over 90 minutes. Concurrently the initiator solution was added over 90 minutes. A nitrogen sparge was continued during these additions. The reaction mixture was then cooked at 85° C. for two hours. The final product was an emulsion composition with 14.4% solids.

Example 71

50.8 grams of a low molecular weight Carboxymethyl cellulose (CMC) (Finnfix 2 from CP Kelco) was dissolved in 686 grams of water in a 1 liter reactor equipped with stirrer and a heating mantle. The mixture was heated to 85° C. while sparging with nitrogen for one hour. A monomer solution containing 50.7 grams of methacrylic acid, 87.6 grams of ethyl acrylate and 0.55 grams of trimethylol propyl triacrylate (TMPTA) was prepared. An initiator solution containing 0.58 grams of ammonium persulfate dissolved in 52 grams of water was prepared. 5 weight percent of the monomer mixture above was added to the reactor and held for 15 minutes. 9 weight percent of the initiator mixture above was added to the reactor and held for 15 minutes. The rest of the monomer was then added over 90 minutes. Concurrently the rest of the initiator solution was added over 90 minutes. A nitrogen sparge was continued during these additions. The reaction mixture was then cooked at 85° C. for an hour and then 2 hours at 70° C. The final product was an emulsion composition with 19.8% solids.

Example 72

103 grams of a crosslinked starch ThermFlo (available from Ingredion) was mixed with 706 grams of water in a reactor equipped with stirrer and a heating mantle. The mixture was heated to 95° C. A solution of 10 grams of 35% hydrogen peroxide in 250 grams of water was added and the reaction mixture was held at 95° C. for 1 hour. The viscosity dropped noticeably in this time. The reaction temperature was dropped to 85° C. and was sparged with nitrogen for one hour. A monomer solution containing containing 101.7 grams of methacrylic acid, 125.9 grams of ethyl acrylate, 0.25 grams of diallylphthalate and 22.5 grams of $C_{16}$ alcohol with 20 EO itaconate (associative monomer) was prepared. 5 weight percent of the monomer mixture above was added to the reactor. Concurrently an initiator solution containing 0.27 grams of ammonium persulfate dissolved in 20 grams of water was added with the monomer solution and held for 15 minutes. The rest of the monomer was then added over 90 minutes. Concurrently an initiator solution containing 0.17 grams of ammonium persulfate dissolved in 45 grams of water was added with the monomer solution. A nitrogen sparge was continued during these additions. The reaction mixture was then cooked at 85° C. for an hour.

Example 73

91.6 grams of 80.9% octenyl succinic anhydride with a water fluidity (WF) of 80 was dissolved in 800 grams of water in a reactor equipped with stirrer and a heating mantle. The mixture was heated to 85° C. while sparging with nitrogen for one hour. A monomer solution containing 27.0 grams of methacrylic acid, 46.7 grams of ethyl acrylate and 0.29 grams of trimethylol propyl triacrylate (TMPTA) was prepared. An initiator solution containing 0.47 grams of ammonium persulfate dissolved in 41.7 grams of water was prepared. The monomer solution was then added over 90 minutes. Concurrently the initiator solution was added over 90 minutes. A nitrogen sparge was continued during these additions. The reaction mixture was then cooked at 85° C. for two hours. The final product was an emulsion composition with 14.4% solids.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described herein, the invention is not intended to be limited to the details shown. Rather, various modifications may be made in the details within the range and scope of equivalents of the claims and without departing from the spirit and scope of the invention.

We claim:

1. A polysaccharide alkali swellable rheology modifier comprising an emulsion polymer comprising at least one polysaccharide portion and at least one synthetic portion, said polysaccharide alkali swellable rheology modifier being obtainable by emulsion polymerizing at least one polysaccharide with at least one anionic ethylenically unsaturated monomer and at least one nonionic ethylenically unsaturated monomer in the presence of an initiating system, the emulsion polymer further comprising at least one associative monomer that is an ethylenically unsaturated monomer containing a hydrophobe and a spacer moiety that spaces the hydrophobe from the backbone of the polymer, wherein the minimum weight of anionic ethylenically unsaturated monomer is about 15 weight percent or more of the total monomer added to the polymerization process, wherein at least one of the at least one nonionic ethylenically unsaturated monomers is a hydrophobic ethylenically unsaturated monomer present in an amount effective to form an emulsion, and wherein when the polysaccharide portion is obtained from cellulose or a cellulose derivative, the cellulose or cellulose derivative has about 0.1% or greater solubility in water at 25° C.

2. The rheology modifier of claim 1 wherein the polysaccharide portion is obtained from a starch or a starch derivative or a cellulose or a cellulose derivative.

3. The rheology modifier of claim 1 wherein the polysaccharide portion is obtained from a starch or starch derivative selected from the group consisting of thermally treated starch, mechanically treated starch, oxidatively degraded starch, hydrolytically degraded starch, enzymatically degraded starch, chemically modified starches and combinations thereof.

4. The rheology modifier of claim 3 wherein the starch derivative is selected from the group consisting of maltodextrin, dextrin, pyrodextrin, oxidized starch, cyclodextrin, substituted cyclodextrins, higher molecular weight starch, hydrogenated starch hydrolyslates and combinations thereof.

5. The rheology modifier of claim 1 wherein the polysaccharide portion is obtained from a cellulose or cellulose derivative selected from the group consisting of carboxymethyl cellulose (CMC), hydroxethyl cellulose (HEC), carboxymethyl hydroxethyl cellulose (CMHEC), hydroxypropyl cellulose (HPC), ethyl hydroxyethyl cellulose (EHEC), methyl ethyl hydroxyethyl cellulose (MEHEC), and hydrophobically modified ethyl hydroxy ethyl celluloses (HM-EHEC) and combinations thereof.

6. The rheology modifier of claim 1 wherein the anionic ethylenically unsaturated monomer is selected from the group consisting of acrylic acid, maleic acid, methacrylic acid, itaconic acid, 2-acrylamido-2-methyl propane sulfonic acid and mixtures thereof.

7. The rheology modifier of claim 1 wherein the hydrophobic ethylenically unsaturated monomer is selected from the group consisting of ethyl (meth)acrylate, methyl (meth) acrylate, 2-ethylhexyl acrylate, butyl (meth)acrylate, vinyl acetate, tertiary butyl acrylamide and combinations thereof.

8. The rheology modifier of claim 1 wherein the hydrophobic ethylenically unsaturated monomer has a water solubility of about less than 3 grams per 100 mls of water at 25° C.

9. The rheology modifier of claim 1 wherein the hydrophobe with the spacer moiety is selected from the group consisting of alcohol ethoxylates, alkylphenoxy ethoxylates, propoxylated/butoxylated ethoxylates and ethoxylated silicones.

10. The rheology modifier of claim 1 wherein the minimum weight percent of the polysaccharide portion is about 5% of the polysaccharide alkali swellable rheology modifier and the maximum weight percent of the polysaccharide portion is about 90% of the polysaccharide alkali swellable rheology modifier.

11. The rheology modifier of claim 1 wherein the rheology modifier has a weight average molecular weight of about 5,000,000 or less.

12. A method of making a polysaccharide alkali swellable rheology modifier comprising:

emulsion polymerizing a polysaccharide with at least one anionic ethylenically unsaturated monomer, and at least one nonionic ethylenically unsaturated monomer in the presence of an initiating system, wherein at least one of the at least one nonionic ethylenically unsaturated monomers is a hydrophobic ethylenically unsaturated monomer and is present in an amount effective to form an emulsion, and wherein the hydrophobic ethylenically unsaturated monomer is present an amount effective to form an emulsion, wherein the minimum weight of anionic ethylenically unsaturated monomer is about 15 weight percent or more of the total monomer added to the polymerization process, and wherein the emulsion polymerization step is conducted substantially free of surfactant.

13. The method of claim 12 wherein the polysaccharide is depolymerized before or during the polymerizing step.

14. A composition comprising the rheology modifier according to claim 1 wherein the composition is selected from the group consisting of a personal care composition, a fabric and cleaning composition, an oil field composition, an agricultural composition, a paint composition and a coating composition.

15. A polysaccharide alkali swellable rheology modifier comprising an emulsion polymer comprising at least one polysaccharide portion and at least one synthetic portion, said polysaccharide alkali swellable rheology modifier being obtainable by emulsion polymerizing at least one polysaccharide with at least one anionic ethylenically unsaturated monomer and at least one nonionic ethylenically unsaturated monomer in the presence of an initiating system, wherein the minimum weight of anionic ethylenically unsaturated monomer is about 15 weight percent or more of the total monomer added to the polymerization process, wherein at least one of the at least one nonionic ethylenically unsaturated monomers is a hydrophobic ethylenically unsaturated monomer present in an amount effective to form an emulsion, wherein when the Polysaccharide portion is obtained from cellulose or a cellulose derivative, the cellulose or cellulose derivative has about 0.1% or greater solubility in water at 25° C., and wherein the emulsion polymer is substantially free of surfactant.

16. A stable emulsion system comprising the polysaccharide alkali swellable rheology modifier of claim 1, unreacted polysaccharide and water, the system comprising at least 10 wt % solids.

17. A stable emulsion system comprising the polysaccharide alkali swellable rheology modifier of claim 15, unreacted polysaccharide and water, the system comprising at least 10 wt % solids.

* * * * *